US012735573B2

(12) United States Patent
Rathnamalala et al.

(10) Patent No.: US 12,735,573 B2
(45) Date of Patent: Sep. 15, 2026

(54) NEAR INFRARED DYES FOR BIOLOGICAL IMAGING AND OPTOELECTRONIC DEVICES

(71) Applicants: Chathuranga S.L. Rathnamalala, Starkville, MS (US); Colleen N. Scott, Starkville, MS (US)

(72) Inventors: Chathuranga S.L. Rathnamalala, Starkville, MS (US); Colleen N. Scott, Starkville, MS (US)

(73) Assignee: Mississippi State University, Starkville, MS (US)

( * ) Notice: Subject to any disclaimer, the term of this patent is extended or adjusted under 35 U.S.C. 154(b) by 405 days.

(21) Appl. No.: 18/470,005

(22) Filed: Sep. 19, 2023

(65) Prior Publication Data

US 2024/0124714 A1 Apr. 18, 2024

Related U.S. Application Data

(60) Provisional application No. 63/376,666, filed on Sep. 22, 2022.

(51) Int. Cl.

*C09B 11/28* (2006.01)
*C07D 409/14* (2006.01)
*C09B 67/20* (2006.01)
*C09K 11/02* (2006.01)
*C09K 11/06* (2006.01)
*G01N 1/30* (2006.01)

(52) U.S. Cl.

CPC ............ *C09B 11/28* (2013.01); *C07D 409/14* (2013.01); *C09B 67/0063* (2013.01); *C09K 11/02* (2013.01); *C09K 11/06* (2013.01); *G01N 1/30* (2013.01); *C09K 2211/1007* (2013.01); *C09K 2211/1018* (2013.01); *G01N 2001/302* (2013.01)

(58) Field of Classification Search

CPC ... C09B 11/28; C09B 67/0063; C07D 409/14; C09K 11/02; C09K 11/06; C09K 2211/1007; C09K 2211/1018; G01N 1/30; G01N 2001/302

See application file for complete search history.

(56) References Cited

U.S. PATENT DOCUMENTS 5,019,480 A 5/1991 DeBoer et al.
5,034,303 A 7/1991 Evans et al.
5,108,873 A 4/1992 Fukui et al.
10,053,484 B2 8/2018 Mao et al.
2022/0056335 A1 2/2022 Delcamp et al.

FOREIGN PATENT DOCUMENTS

CA 2613386 C 5/2015
EP 2007589 B1 6/2011

OTHER PUBLICATIONS

Rajapaksha, Ishanka, et al. "New design strategy toward NIR I xanthene-based dyes." The Journal of Organic Chemistry 85.19 (2020): 12108-12116. (Year: 2020).*

Rathnamalala, Chathuranga S.L., et al. "Donor-Acceptor-Donor NIR II Emissive Rhodindolizine Dye Synthesized by C—H Bond Functionalization." The Journal of Organic Chemistry 84.20 (2019): 13186-13193.

Rathnamalala, Chathuranga SL, et al. "Thienylpiperidine Donor NIR Xanthene-Based Dye for Photoacoustic Imaging." Organic Letters 23.19 (2021): 7640-7644.

Liu, Feng, et al. "Engineering an NIR rhodol derivative with spirocyclic ring-opening activation for high-contrast photoacoustic imaging." Chemical Science 10.40 (2019): 9257-9264.

Wang, Sheng, et al. "Ratiometric Photoacoustic Nanoprobe for Bioimaging of Cu2+." ACS Applied Materials & Interfaces 11.2 (2019): 1917-1923.

Attia, Amalina Binte Ebrahim, et al. "A review of clinical photoacoustic imaging: Current and future trends." Photoacoustics 16 (2019): 100144.

(Continued)

*Primary Examiner* — James H Alstrum-Acevedo
*Assistant Examiner* — Justin Christopher Sanchez
(74) *Attorney, Agent, or Firm* — Mendelsohn Dunleavy P.C.; Kevin J. Dunleavy

(57) ABSTRACT

A near infrared dye comprising a counterion and a structure of Formula I

Formula I

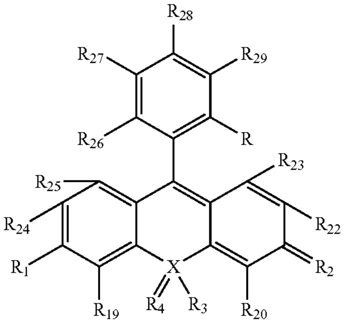

wherein the at least one of $R_1$ and $R_2$ are 1-(thiophen-2-yl) piperidine, 1-(thieno[3,2-b]thiophen-2-yl)piperidine or 1-([2,2'-bithiophen]-5-yl)piperidine, and X, R, $R_3$-$R_4$, $R_{19}$, $R_{20}$ and $R_{22}$-$R_{29}$ are disclosed herein. Materials and compositions comprising the NIR dye can absorb light in the NIR I & II regions and then the energy can be released in the form of light (fluorescence) or heat (non-radiative). The dyes can also convert the absorbed light to heat and ultrasound waves via the photoacoustic effect. The photoacoustic effect can be used in photoacoustic tomography to image biological materials or processes. Methods for synthesizing the NIR dyes and materials comprising the same are also disclosed.

20 Claims, 10 Drawing Sheets

(56) References Cited

OTHER PUBLICATIONS

Liu, Chuangjun, et al. "Design strategies to rhodamine analogue fluorophores for near-infrared II biological imaging applications." Dyes and Pigments 196 (2021): 109792.
Rajapaksha, Ishanka, et al. "New Design Strategy toward NIR I Xanthene-Based Dyes." The Journal of Organic Chemistry 85.19 (2020): 12108-12116.
Wang, Lihong V., et al. "Photoacoustic Tomography: In Vivo Imaging from Organelles to Organs." Science 335.6075 (2012): 1458-1462.
Kanazaki, Kengo, et al. "Development of human serum albumin conjugated with near-infrared dye for photoacoustic tumor imaging." Journal of Biomedical Optics 19.9 (2014): 096002-096002.
Teraphongphom, Nutte, et al. "Specimen Mapping in Head and Neck Cancer Using Fluorescence Imaging." Laryngoscope Investigative Otolaryngology 2.6 (2017): 447-452.
Merkes, Jean Michél, et al. "Tuning Optical Properties of Bodipy Dyes by Pyrrole Conjugation for Photoacoustic Imaging." Advanced Optical Materials 8.11 (2020): 1902115.
Shi, Ben, et al. "Photoacoustic probes for real-time tracking of endogenous H2S in living mice." Chemical Science 8.3 (2017): 2150-2155.
Ikeno, Takayuki, et al., "Design and Synthesis of an Activatable Photoacoustic Probe for Hypochlorous Acid." Analytical Chemistry 91.14 (2019): 9086-9092.
Horvath, Thomas D., et al. "Ratiometric photoacoustic sensing of pH using a "sonophore"." Analyst 133.6 (2008): 747-749.
Kinnibrugh, Tiffany L., et al. "Dipolar Second-Order Nonlinear Optical Chromophores Containing Ferrocene, Octamethylferrocene, and Ruthenocene Donors and Strong π-Acceptors: Crystal Structures and Comparison of π-Donor Strengths." Organometallics 28.5 (2009): 1350-1357.
Qian, Gang, et al. "Near-Infrared Organic Compounds and Emerging Applications." Chemistry—An Asian Journal 5.5 (2010): 1006-1029.
Lu, Zhikuan, et al. "A mild and practical copper catalyzed amination of halothiophenes." Tetrahedron 61.4 (2005): 903-918.
Roger, Julien, et al. "Aryl triflates: useful coupling partners for the direct arylation of heteroaryl derivatives via Pd-catalyzed C—H activation-functionalization." Organic & Biomolecular Chemistry 6.1 (2008): 169-174.
Ou, Changjin, et al. "A three-dimensional Bodipy-iron (iii) compound with improved H2O2-response for NIR-II photoacoustic imaging guided chemodynamic/photothermal therapy." Chemical Communications 56.46 (2020): 6281-6284.
Zhou, Effie Y., et al. "A Conformationally Restricted Aza-Bodipy Platform for Stimulus-Responsive Probes with Enhanced Photoacoustic Properties." Journal of the American Chemical Society 141.44 (2019): 17601-17609.
An, Fei-Fei, et al. "Aggregation-Induced Near-Infrared Absorption of Squaraine Dye in an Albumin Nanocomplex for Photoacoustic Tomography in Vivo." ACS Applied Materials & Interfaces 6.20 (2014): 17985-17992.
Yao, Defan, et al. "Molecular Engineered Squaraine Nanoprobe for NIR-II/Photoacoustic Imaging and Photothermal Therapy of Metastatic Breast Cancer." ACS Applied Materials & Interfaces 12.4 (2020): 4276-4284.
Lovell, Jonathan F., et al. "Porphysome nanovesicles generated by porphyrin bilayers for use as multimodal biophotonic contrast agents." Nature Materials 10.4 (2011): 324-332.
Shimomura, Keito, et al. "Bis-Metal Complexes of Doubly N Confused Dioxohexaphyrins as Potential Near-Infrared-II Photoacoustic Dyes." Journal of the American Chemical Society 142.9 (2020): 4429-4437.
Zheng, Xiaohua, et al. "Nanoparticles of Chlorin Dimer with Enhanced Absorbance for Photoacoustic Imaging and Phototherapy." Advanced Functional Materials 28.26 (2018): 1706507.
Merkes, Jean Michél, et al. "Photoacoustic Detection of Superoxide Using Oxoporphyrinogen and Porphyrin." ACS Sensors 4.8 (2019): 2001-2008.
Li, Xiang, et al. "A small-molecule probe for ratiometric photoacoustic imaging of hydrogen sulfide in living mice." Chemical Communications 55.42 (2019): 5934-5937.
Gao, Wen, et al. "A Redox-Responsive Self-Assembled Nanoprobe for Photoacoustic Inflammation Imaging to Assess Atherosclerotic Plaque Vulnerability." Analytical Chemistry 91.1 (2018): 1150-1156.
Lu, Yuansheng, et al. "New frog-type Dibenzo[a,c][1,2,5]thiadiazolo[3,4-i]phenazine heterocyclic derivatives with aggregation 10 enhanced one-and two-photon excitation NIR fluorescence." Dyes and Pigments 153 (2018): 233-240.
Zhang, Ruiping, et al. "Rational Design of a Multifunctional Molecular Dye with Single Dose and Laser for Efficiency NIR-II Fluorescence/Photoacoustic Imaging Guided Photothermal Therapy." Analytical Chemistry 91.19 (2019): 12476-12483.
Jo, Janggun, et al. "In vivo quantitative imaging of tumor pH by nanosonophore assisted multispectral photoacoustic imaging." Nature communications 8.1 (2017): 471.
Matsui, Masaki, et al. "UV-vis absorption and fluorescence spectra, solvatochromism, and application to pH sensors of novel xanthene dyes having thienyl and thieno [3, 2-b] thienyl rings as auxochrome." Dyes and Pigments 139 (2017): 533-540.
Chai, Jeng-Da, and Martin Head-Gordon. "Long-range corrected hybrid density functionals with damped atom-atom dispersion corrections." Physical Chemistry Chemical Physics 10.44 (2008): 6615-6620.
Rappoport, Dmitrij, et al. "Property-optimized Gaussian basis sets for molecular response calculations." The Journal of Chemical Physics 133.13 (2010).
Humphrey, William, et al. "VMD: Visual Molecular Dynamics." Journal of Molecular Graphics 14.1 (1996): 33-38.
Forman, Henry Jay, et al. "Glutathione: Overview of its protective roles, measurement, and biosynthesis." Molecular Aspects of Medicine 30.1-2 (2009): 1-12.

* cited by examiner

NEAR INFRARED DYES FOR BIOLOGICAL IMAGING AND OPTOELECTRONIC DEVICES

CROSS-REFERENCE TO RELATED APPLICATIONS

This application claims priority to U.S. provisional application No. 63,376,666, filed on Sep. 22, 2022, the disclosure of which is hereby incorporated by reference in its entirety as if fully set forth herein.

STATEMENT OF GOVERNMENT INTEREST

This invention was made with government support under grant number 01A-1757220, awarded by the National Science Foundation. The government has certain rights in this invention.

FIELD OF INVENTION

This invention relates generally to the field of dye material and, more particularly, to novel dye materials and compositions that absorb light in the NIR I & II regions and then can be released in the form of light (fluorescence), heat (non-radiative), and ultrasound waves (photoacoustic) effects and methods for synthesizing such materials.

BACKGROUND

Materials in the near-infrared I (NIR I) (~0.7 μm-0.9 μm) and near-infrared II (NIR II) (~0.9 μm-1.7 μm) region of the electromagnetic spectrum have applications in the biomedical imaging field to study biological processes such as in vivo imaging of tumor angiogenesis monitoring, blood oxygenation mapping, functional brain imaging, skin melanoma detection, methemoglobin measuring, etc.

A state-of-the-art biomedical imaging technique is photoacoustic (PA) tomography that is characterized by the conversion of absorbed light to heat and then ultrasound waves via the photoacoustic effect. Following irradiation of an optical absorber, the excited state can relax at a longer wavelength or lower energy via either by emission of a photon (fluorescence, Fl) or via non-radiative decay (photoacoustic). By pulsing the light source, pressure waves caused by thermoelastic expansion and contraction can be detected by ultrasound transducers and converted to high-resolution images. Since sound can readily propagate through tissue with minimal perturbation, PA tomography enables whole-body imaging of animals (e.g., mice), as well as human tissue (e.g., breast). In addition to a low fluorescent quantum yield (<5%) and a large extinction coefficient ($>10^4\ M^{-1}cm^{-1}$), the intensity of the PA output relies on incident light reaching the optical absorber. While any wavelength of light can induce the generation of a PA signal, absorbance above 650 nm is optimal for biological applications since the attenuation and scattering of incident light is minimal. For instance, in an optical imaging study, it was demonstrated that visible light at 510 nm can penetrate 1.5 mm into tissue, whereas light in the far-red (650 nm) and near infrared (>800 nm) regions can reach depths of 3 mm and 5-10 mm, respectively. Consequently, NIR dyes that absorb over 800 nm are desirable for deep tissue imaging. Conversely, should the energy released during relaxation produce light, this process (fluorescence) can also be used to produce images. As with PA imaging, fluorescence at wavelengths in the NIR region can penetrate deeper into tissues to produce images.

Several NIR organic dyes have been explored for imaging, such as 4,4-difluoro-4-bora-3a,4a-diaza-s-indacene (BODIPYs), squaraine, phthalocyanine and porphyrine, cyanines, benzo[c]heterocycles, and xanthene derivatives. Among these, xanthene-based dyes are popular because of the tunability of their remarkable photophysical properties using organic synthesis.

However, xanthene-based probes in the NIR region with absorbance >800 nm are scarce. A rhodol nanoprobe with absorbance at 830 nm used for the ratiometric determination of $Cu^{2+}$ was reported by Wang et al. (Wang et al., ACS Appl. Mater. Interfaces 2019, 11 (2), 1917-1923).[19] To our knowledge, this probe is the only reported xanthene-based PA probe with an absorption wavelength over 800 nm. On the other hand, a few xanthene-based NIR probes with absorption wavelength >800 nm have been reported. (Liu and Scott, *Dyes and Pigments* 196 (2021) 109792). Once recent example by Liu et al. (Liu et al. J Am. Chem. Soc. 2021, 143, 17136-17143) demonstrated the practicality of xanthene-based NIR-II dyes with fluorescence emission at 1210 nm to perform In Vivo dynamic imaging of blood circulation. This is one of the longest wavelengths (NIR II) xanthene-based emissive dye reported to date.

In general, most xanthene-based probes with absorption wavelength over 800 nm have very low fluorescent quantum yields, and/or require arduous synthetic routes for their preparation. Due to the low fluorescent quantum yield, NIR dyes with high molar absorptivity are especially important. With the limited quantities of xanthene-based probes available with absorbance over 800 nm and with the challenges that exist to prepare them in a facile and efficient way, there is a need for easily accessible NIR xanthene-based probes that can access imaging depths on the cm scale, high molar absorptivity, and are highly photostable for PA or fluorescence applications. The present disclosure addresses these needs.

SUMMARY

In an aspect, the disclosure relates to a near infrared (NIR) dye comprising a counterion and a structure of Formula I Formula I

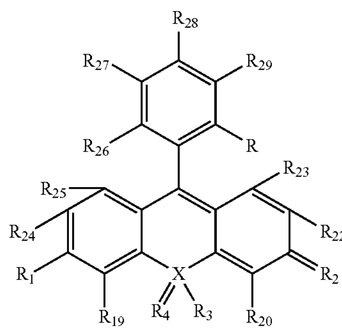

wherein X can be selected from O, Si and P;

R can be selected from hydrogen, —C(O)OH, a substituted or unsubstituted linear or branched $C_1$-$C_{18}$ alkyl group, a substituted or unsubstituted linear or branched $C_2$-$C_{18}$ alkenyl group, a substituted or unsubstituted $C_3$-$C_{10}$ cycloalkyl group, a substituted or unsubstituted linear or branched $C_1$-$C_{18}$ alkoxy group, an ester group represented by the formula —C(O)OA$^1$, wherein A$^1$ can be a substituted or unsubstituted linear or branched $C_1$-$C_{18}$ alkyl group, a substituted or unsubstituted linear or branched $C_2$-$C_{18}$ alkenyl group or a substituted or unsubstituted $C_3$-$C_{10}$ cycloalkyl group, an amide group represented by the formula —C(O)N(A$^2$)$_2$, wherein A$^2$ can be selected from a substituted or unsubstituted linear or branched $C_1$-$C_{18}$ alkyl group, a substituted or unsubstituted linear or branched $C_2$-$C_{18}$ alkenyl group, or a substituted or unsubstituted $C_3$-$C_{10}$ cycloalkyl group, or an ether group represented by the formula —$CH_2OA^3$ wherein A$^3$ can be independently selected from a substituted or unsubstituted linear or branched $C_1$-$C_{18}$ alkyl group, a substituted or unsubstituted linear or branched $C_2$-$C_{18}$ alkenyl group, or a or a substituted or unsubstituted $C_3$-$C_{10}$ cycloalkyl group;

when X can be O, then $R_3$ and $R_4$ can be absent, and when X can be Si, then $R_3$ and $R_4$ can be each singly bonded to the Si atom, and can be independently selected from, hydrogen, a substituted or unsubstituted $C_1$-$C_{18}$ linear or branched alkyl group or a substituted or unsubstituted $C_3$-$C_{10}$ cycloalkyl group, when X can be P, then $R_3$ can be singly bonded to the P atom and can be selected from hydrogen, a substituted or unsubstituted $C_1$-$C_{18}$ linear or branched alkyl group or a substituted or unsubstituted $C_3$-$C_{10}$ cycloalkyl group can be P, and $R_4$ can be singly bonded to the P and can be a substituted or unsubstituted $C_1$-$C_{18}$ linear or branched alkyl group or a substituted or unsubstituted $C_3$-$C_{10}$ cycloalkyl group or $R_4$ can be doubly bonded to the P and can be an oxygen;

wherein $R_{19}$, $R_{20}$, $R_{22}$, $R_{23}$, $R_{24}$, $R_{25}$, $R_{26}$, $R_{27}$, $R_{28}$, and $R_{29}$ can be each independently selected from hydrogen, sulfonate, halogen, hydroxy, amino, nitro, cyano, carboxy, an alkyl group having 1 to 20 carbon atoms, alkenyl group having 2 to 20 carbon atoms, alkynyl group having 2 to 20 carbon atoms, an aryl group having 6 to 10 carbon atoms, a heterocyclic group having 3 to 16 carbon atoms, an alkylether having 2 to 20 carbon atoms and 1 to 5 oxygen atoms, and an alkoxy group having 1 to 20 carbon atoms or wherein one or more pair of $R_{22}$ and $R_{23}$, $R_{24}$ and $R_{25}$, $R_{25}$ and $R_{26}$, $R_{26}$ and $R_{27}$, $R_{27}$ and $R_{28}$, $R_{28}$ and $R_{29}$, together with the carbons they are attached can form a saturated or unsaturated 6 membered ring; and $R_1$ and $R_2$ can be both selected from one of the following Groups A, B and C:

Group A $R_1$ can be hydrogen and $R_2$ can be a donor which can be substituted or unsubstituted and can be a 1-(thiophen-2-yl) piperidine, 1-(thieno[3,2-b]thiophen-2-yl)piperidine or 1-([2,2'-bithiophen]-5-yl)piperidine; or Group B (Symmetrical Dyes)

both $R_1$ and $R_2$ can be the same donors and both can be substituted or unsubstituted, and can be selected from 1-(thiophen-2-yl)piperidine group, 1-(thieno[3,2-b]thiophen-2-yl)piperidine, and 1-([2,2'-bithiophen]-5-yl)piperidine; or Group C (Unsymmetrical Dyes)

$R_1$ and $R_2$ can be different donors and $R_1$ can be a donor, which can be substituted or unsubstituted and can be a 1-(thiophen-2-yl)piperidine, 1-(thieno[3,2-b]thiophen-2-yl) piperidine or 1-([2,2'-bithiophen]-5-yl)piperidine and $R_2$ can be a donor which can be substituted or unsubstituted and can be selected from 1-(thiophen-2-yl)piperidine, 1-(thieno[3,2-b]thiophen-2-yl)piperidine, 1-([2,2'-bithiophen]-5-yl)piperidine, $C_2$-$C_{12}$ dialkyl amino, indolizine-3-yl, diphenylamino, and julolidinyl. In Group C, the dyes are unsymmetrical. For instance, the donor at $R_1$ could be 1-(thiophen-2-yl)piperidine and at $R_2$ could be 1-(thieno[3,2-b]thiophen-2-yl)piperidine; or both $R_1$ and $R_2$ can be 1-(thiophen-2-yl)piperidine but one is substituted and the other is not.

In the foregoing embodiment, X can be O, and $R_3$ and $R_4$ can be absent;

R can be —C(O)OH, or

R can be an ester group, an amide group, or an ether group and A$^1$, A$^2$, and A$^3$ can be independently selected from a linear or branched $C_1$-$C_{18}$ alkyl group, a linear or branched $C_2$-$C_{18}$ alkenyl group, or a $C_3$-$C_{10}$ cycloalkyl group that can be substituted with 1 to 3 substituents independently selected from a halogen, sulfonate, hydroxy, amino, nitro, cyano, carboxy, an alkyl group having 1 to 20 carbon atoms, alkenyl group having 2 to 20 carbon atoms, alkynyl group having 2 to 20 carbon atoms, an aryl group having 6 to 10 carbon atoms, a heterocyclic group having 3 to 16 carbon atoms, and an alkoxy group having 1 to 20 carbon atoms.

In each of the foregoing embodiments, X can be O, and $R_3$ and $R_4$ can be absent;

R can be —C(O)OH or an ester group represented by the formula —C(O)OA$^1$ wherein A$^1$ and A 2 can be independently selected from a linear or branched $C_1$-$C_6$ alkyl group;

$R_1$ and $R_2$ can be both selected from one of the following Groups A and B:

Group A $R_1$ can be hydrogen and $R_2$ can be a donor which can be substituted with 0 to 3 substituents and can be a 1-(thiophen-2-yl)piperidine, 1-(thieno[3,2-b]thiophen-2-yl)piperidine or 1-([2,2'-bithiophen]-5-yl)piperidine; or Group B Both $R_1$ and $R_2$ can be the same donors and both can be substituted with 0 to 3 substituents, and can be selected from 1-(thiophen-2-yl)piperidine group, 1-(thieno[3,2-b]thiophen-2-yl)piperidine, and 1-([2,2'-bithiophen]-5-yl)piperidine;

wherein the substituents can be independently selected from a halogen, sulfonate, hydroxy, amino, nitro, cyano, carboxy, an alkyl group having 1 to 20 carbons, alkenyl group having 2 to 20 carbon atoms, alkynyl group having 2 to 20 carbon atoms, an alkylether having 2-20 carbon atoms and 1 to 5 oxygen atoms, an aryl group having 6 to 10 carbon atoms, a heterocyclic group having 3 to 16 carbons, and an alkoxy group having 1 to 20 carbon atoms.

In each of the foregoing embodiments, X can be O, and $R_3$ and $R_4$ can be absent;

R can be —C(O)OH or an ester group represented by the formula —C(O)OA$^1$ wherein A$^1$ and A$^2$ can be independently selected from a linear or branched $C_1$-$C_6$ alkyl group;

$R_1$ and $R_2$ can be both selected from Group C:

Group C $R_1$ and $R_2$ can be different donors and $R_1$ can be a donor which can be substituted with 0 to 3 substituents and can be a 1-(thiophen-2-yl)piperidine, 1-(thieno[3,2-b]thiophen-2-yl)piperidine or 1-([2,2'-bithiophen]-5-yl)piperidine and $R_2$ can be a donor which can be substituted with 0 to 3 substituents, and can be selected from 1-(thiophen-2-yl) piperidine, 1-(thieno[3,2-b]thiophen-2-yl)piperidine, 1-([2, 2'-bithiophen]-5-yl)piperidine, $C_2$-$C_{12}$ dialkyl amino, indolizine-3-yl, diphenylamino, and julolidinyl;

wherein the substituents can be independently selected from a halogen, sulfonate, hydroxy, amino, nitro, cyano, carboxy, an alkyl group having 1 to 20 carbon atoms, alkenyl group having 2 to 20 carbon atoms, alkynyl group having 2 to 20 carbon atoms, an alkylether having 2 to 20 carbon atoms and 1 to 5 oxygen atoms, an aryl group having 6 to 10 carbon atoms, a heterocyclic group having 3 to 16 carbon atoms, and an alkoxy group having 1 to 20 carbon atoms.

In each of the foregoing embodiments, X can be O, and $R_3$ and $R_4$ can be absent;

R can be —C(O)OH or an ester group represented by the formula —C(O)OA$^1$ wherein A$^1$ and A$^2$ can be independently selected from a linear or branched $C_1$-$C_6$ alkyl group;

$R_1$ and $R_2$ can be both selected from Group C:

Group C $R_1$ and $R_2$ can be different donors and $R_1$ can be a donor which can be substituted with 0 to 3 substituents and can be a 1-(thiophen-2-yl)piperidine, 1-(thieno[3,2-b]thiophen-2-yl)piperidine or 1-([2,2'-bithiophen]-5-yl)piperidine and $R_2$ can be a donor which can be substituted with 0 to 3 substituents and can be selected from 1-(thiophen-2-yl) piperidine, 1-(thieno[3,2-b]thiophen-2-yl)piperidine, 1-([2, 2'-bithiophen]-5-yl)piperidine, diethyl amino, and julolidinyl;

wherein the substituents can be independently selected from a halogen, sulfonate, hydroxy, amino, nitro, cyano, carboxy, an alkyl group having 1 to 20 carbon atoms, alkenyl group having 2 to 20 carbon atoms, alkynyl group having 2 to 20 carbon atoms, an alkylether having 2 to 20 carbon atoms and 1 to 5 oxygen atoms, an aryl group having 6 to 10 carbon atoms, a heterocyclic group having 3 to 16 carbon atoms, and an alkoxy group having 1 to 20 carbon atoms.

In each of the foregoing embodiments, the counterion can be nitrite, sulfate, phosphate, bicarbonate, trifluoroacetate, pentafluoropropanoate, chloride, bromide, iodide, perchlorate, nitrate, benzenesulfonate, p-toluenesulfonate, methyl sulfate, ethyl sulfate, propyl sulfate, tetrafluoroborate, tetraphenylborate, hexafluorophosphate, benzenesulfinate, acetate, trifluoroacetate, propionacetate, benzoate, oxalate, succinate, malonate, oleate, stearate, citrate, monohydrogen diphosphate, dihydrogen monophosphate, pentachlorostannate, chlorosulfonate, fluorosulfonate, trifluoromethansulfonate, hexafluoroarsenate, hexafluoroantimonate, molybdenate, tungstate, titanate, zirconate ions, or any combination thereof.

In each of the foregoing embodiments, the counterion can be trifluoroacetate, pentafluoropropanoate, chloride, bromide, iodide, fluorosulfonate, and trifluoromethansulfonate.

In each of the foregoing embodiments, $R_{19}$, $R_{20}$, $R_{22}$, $R_{23}$, $R_{24}$, $R_{25}$, $R_{26}$, $R_{27}$, $R_{28}$, and $R_{29}$ can be each independently selected from hydrogen, sulfonate, halogen, hydroxy, amino, nitro, cyano, carboxy, an alkyl group having 1 to 6 carbon atoms, alkenyl group having 2 to 6 carbon atoms, an alkylether having 2 to 20 carbon atoms and 1 to 5 oxygen atoms, an aryl group having 6 to 10 carbon atoms, a heterocyclic group having 6 to 10 carbon atoms, and wherein 0 or 1 pair of $R_{22}$ and $R_{23}$, $R_{24}$ and $R_{25}$, $R_{25}$ and $R_{26}$, $R_{26}$ and $R_{27}$, $R_{27}$ and $R_{28}$, $R_{28}$ and $R_{29}$, together with the carbons they are attached from can form a saturated or unsaturated 6 membered ring.

In each of the foregoing embodiments, $R_{19}$, $R_{20}$, $R_{22}$, $R_{23}$, $R_{24}$, $R_{25}$, $R_{26}$, $R_{27}$, $R_{28}$, and $R_{29}$ can be each independently selected from hydrogen, sulfonate, halogen, hydroxy, an alkyl group having 1 to 6 carbon atoms, and a phenyl.

In each of the foregoing embodiments, $R_{19}$, $R_{20}$, $R_{22}$, $R_{23}$, $R_{24}$, $R_{25}$, $R_{26}$, $R_{27}$, $R_{28}$, and $R_{29}$ can be each hydrogen.

In each of the foregoing embodiments, the NIR dye can have one of the following structures:

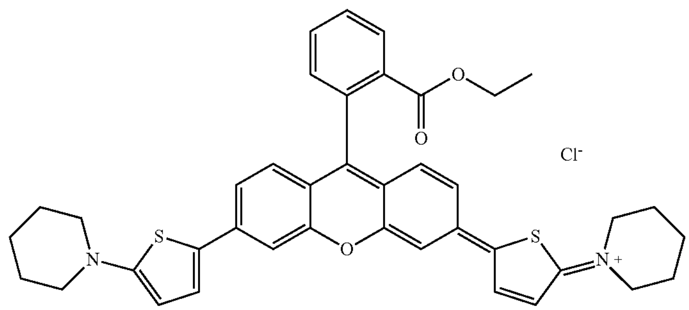

,

XanthCR-880

-continued

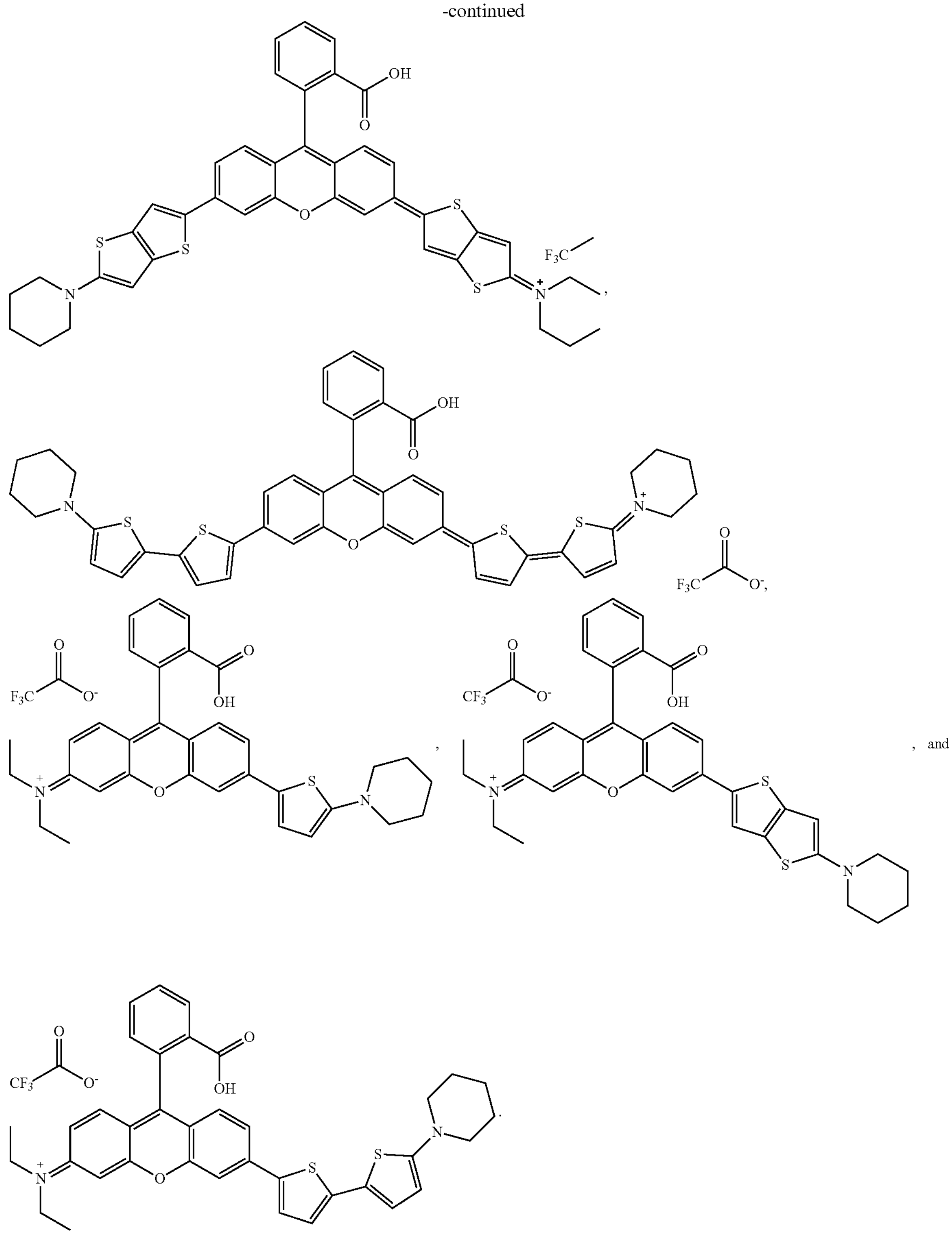

, and

The IR absorbance spectra of the above-NIR dyes is shown in FIGS. 5A-5E.

In each of the foregoing embodiments, the NIR dye can absorb light in the NIR I region and/or the NIR II region; or wherein the NIR dye can absorb light in the NIR II region; or wherein the NIR dye can have an absorption maximum in the NIR II region.

In another aspect of the disclosure is a composite comprising the NIR dye of any one of foregoing embodiments in a polymer matrix. Preferably, the polymer matrix can be solid at room ternperature.

In yet another aspect of the disclosure is a method for making a NIR dye, the method comprising:

(a) performing a C—H arylation reaction by combining a Donor and an Acceptor of Formula II with a catalyst in a solvent to form a reaction mixture, Formula II

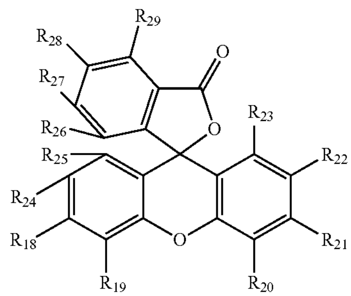

wherein $R_{18}$ and $R_{21}$ can be individually selected from Cl, Br, I and $OSO_2R_{52}$ wherein $R_{52}$ can be a hydrogen or lower alkyl;

wherein $R_{19}$, $R_{20}$, $R_{22}$, $R_{23}$, $R_{24}$, $R_{25}$, $R_{26}$, $R_{27}$, $R_{28}$, and $R_{29}$ can be each independently selected from hydrogen or an alkyl group having 1 to 20 carbons, or wherein one or more pair of $R_{22}$ and $R_{23}$, $R_{24}$ and $R_{25}$, $R_{25}$ and $R_{26}$, $R_{26}$ and $R_{27}$, $R_{27}$ and $R_{28}$, $R_{28}$ and $R_{29}$, together with the carbons they are attached can form a saturated or unsaturated 6 membered ring; and wherein the Donor(s) can be substituted or unsubstituted and comprises at least one from Group (X) and one from Group (Y):

(X) 1-(thiophen-2-yl)piperidine, 1-(thieno[3,2-b]thiophen-2-yl)piperidine or 1-([2,2'-bithiophen]-5-yl)piperidine; and (Y) 1-(thiophen-2-yl)piperidine, 1-(thieno[3,2-b]thiophen-2-yl)piperidine, 1-([2,2'-bithiophen]-5-yl)piperidine, $C_2$-$C_{12}$ dialkyl amine, indolizine, diphenylamine, and julolidine, to thereby replace the groups at $R_{18}$ and $R_{21}$ with said Donor(s);

(b) a ring opening reaction by transesterification with an alcohol to give the NIR dyes of Formula I Formula I

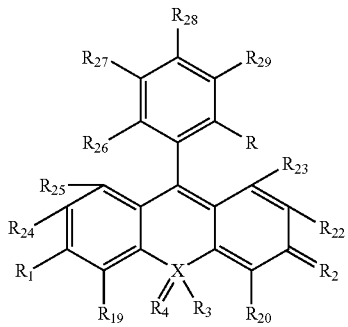

wherein X can be O, and $R_3$ and $R_4$ are absent;

R can be selected from —C(O)OH or an ester group represented by the formula —C(O)O$A^1$, wherein $A^1$ can be a linear or branched $C_1$-$C_{18}$ alkyl group;

wherein $R_{19}$, $R_{20}$, $R_{22}$, $R_{23}$, $R_{24}$, $R_{25}$, $R_{26}$, $R_{27}$, $R_{28}$, and $R_{29}$ can be as described above; and $R_1$ and $R_2$ can be both selected from one of the following Groups B and C:

Group B (Symmetrical Dyes)

both $R_1$ and $R_2$ can be the same donors, and both can be substituted or unsubstituted, and can be selected from 1-(thiophen-2-yl)piperidine group, 1-(thieno[3,2-b]thiophen-2-yl)piperidine, and 1-([2,2'-bithiophen]-5-yl)piperidine; or Group C (Unsymmetrical Dyes)

$R_1$ and $R_2$ can be different donors and $R_1$ can be a donor which can be substituted or unsubstituted and can be a 1-(thiophen-2-yl)piperidine, 1-(thieno[3,2-b]thiophen-2-yl)piperidine or 1-([2,2'-bithiophen]-5-yl)piperidine and $R_2$ can be a donor which can be substituted or unsubstituted and can be selected from 1-(thiophen-2-yl)piperidine, 1-(thieno[3,2-b]thiophen-2-yl)piperidine, 1-([2,2'-bithiophen]-5-yl)piperidine, $C_2$-$C_{12}$ dialkyl amino, indolizine-3-yl, diphenylamino, and julolidinyl. In Group C, the dyes are unsymmetrical. For instance, the donor at $R_1$ could be 1-(thiophen-2-yl)piperidine and at $R_2$ could be 1-(thieno[3,2-b]thiophen-2-yl)piperidine; or both $R_1$ and $R_2$ can be 1-(thiophen-2-yl)piperidine but one is substituted and the other is not.

In the foregoing embodiment, the catalyst in step (a) can be a palladium compound.

In each of the foregoing embodiments, the compound of Formula II can be as follows:

2

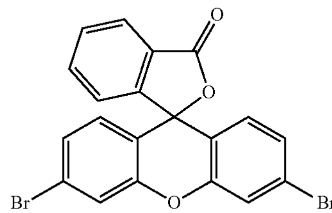

In each of the foregoing embodiments, the compound formed in step (a) can have the following structure:

3

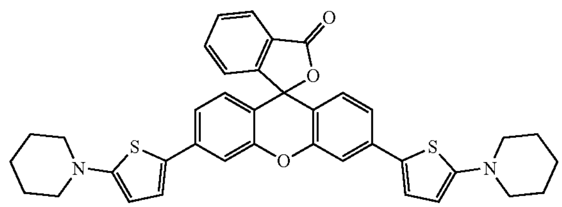

In yet another aspect of the disclosure is a composition comprising the NIR dyes of any one of the foregoing embodiments and a pharmaceutically-acceptable carrier or a solid polymer matrix.

In yet another aspect of the disclosure is a method for imaging a biological sample, the method comprising:

(a) contacting the biological sample with an effective amount of the composition of as disclosed in each of the foregoing embodiments;

(b) exposing the biological sample and the composition to NIR radiation; and (c) observing photoacoustic resonance or fluorescence in the biological sample.

Figure 1:
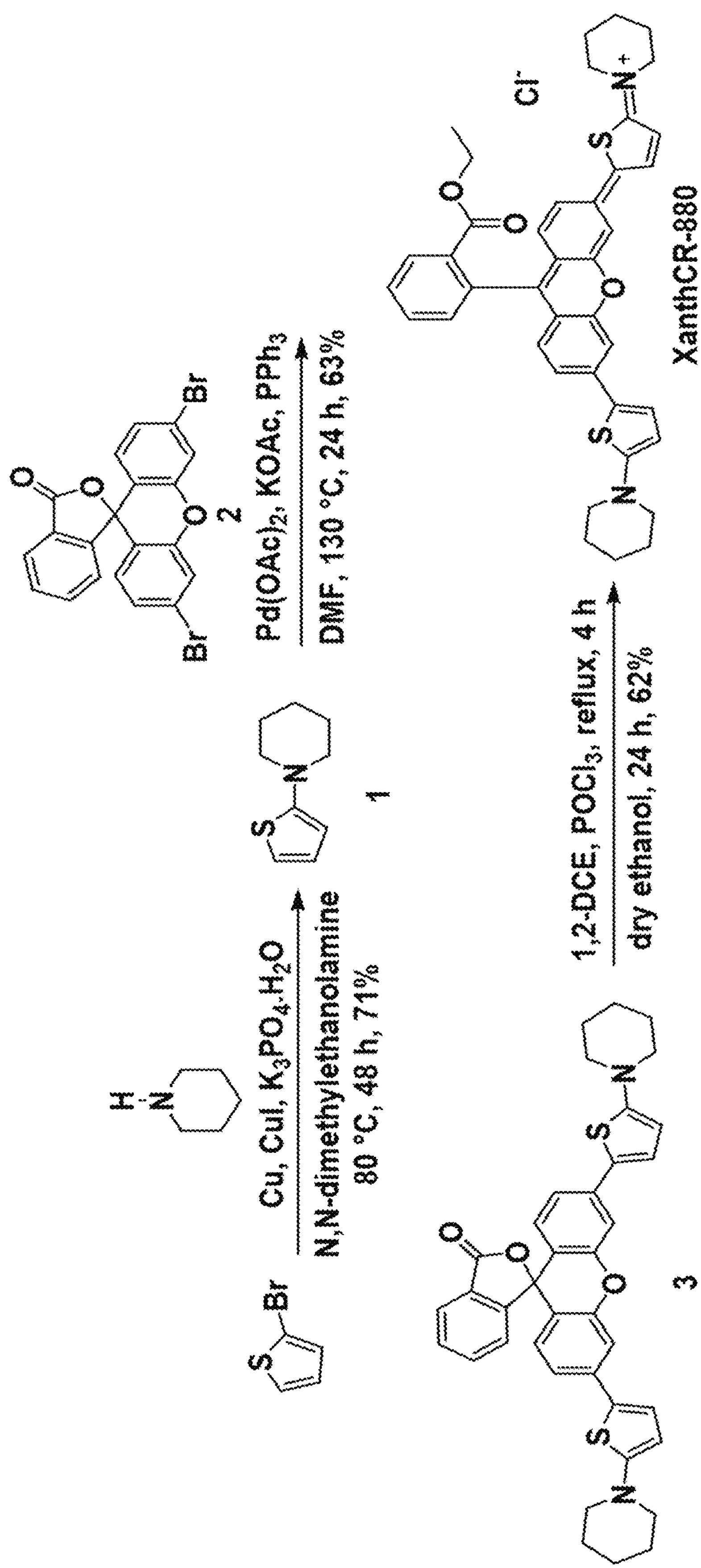
FIG. 1 shows the synthesis of 1-{5-[(3E)-9-[2-(Ethoxycarbonyl)phenyl]-6-[5-(piperidin-1-yl)thiophen-2-yl]-3H- xanthen-3-ylidene]-2,5-dihydrothiophen-2-ylidene}-1λ5-piperidin-1-ylium chloride (XanthCR-880) wherein an intermediate is in the closed form (3).
Figure 2:
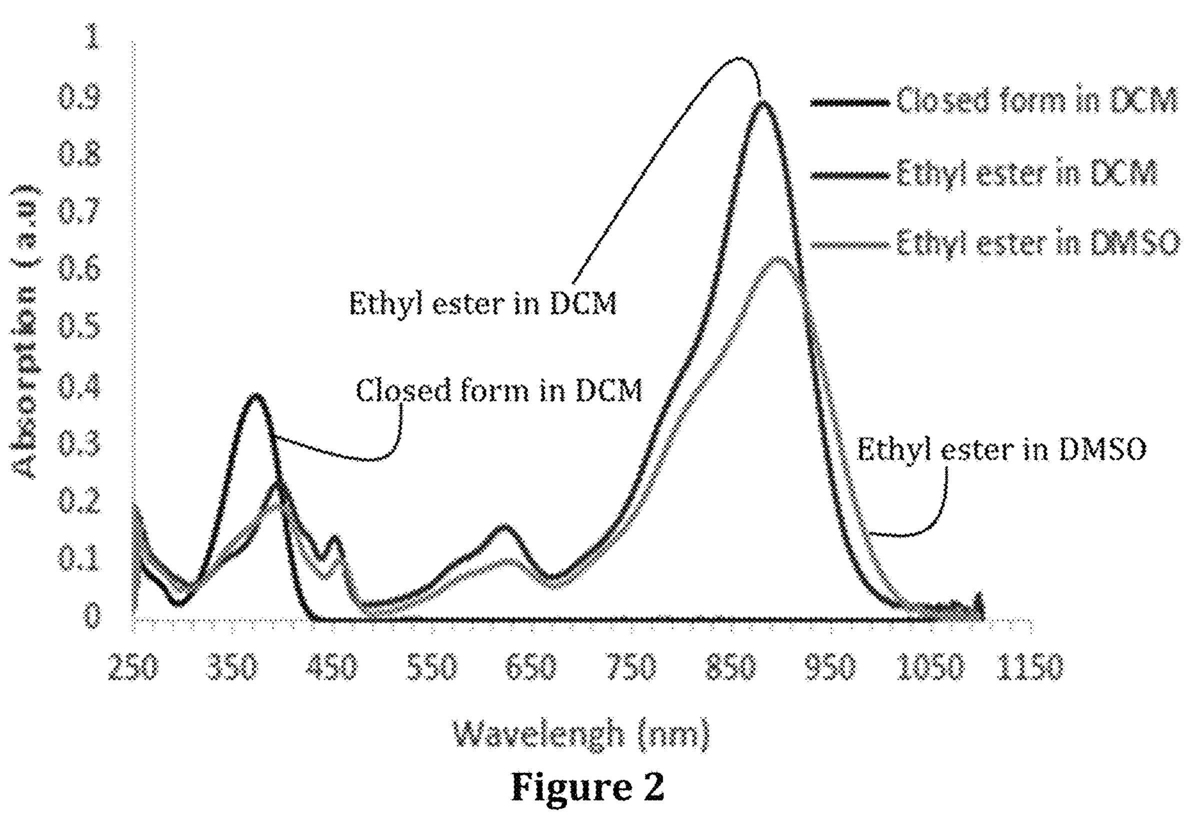

FIG. 2 shows the UV absorption spectra of 10 μM solution for the closed form (3) and ethyl ester XanthCR-880 version of the dye as described in FIG. 1.

Figure 3A:
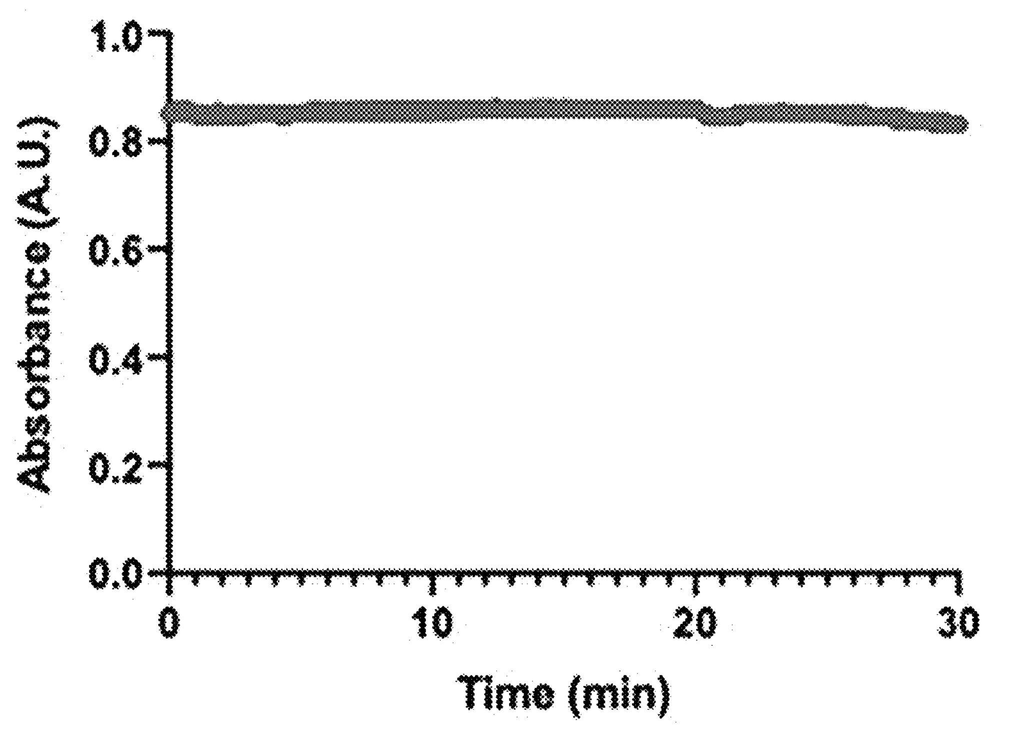
Figure 3B:
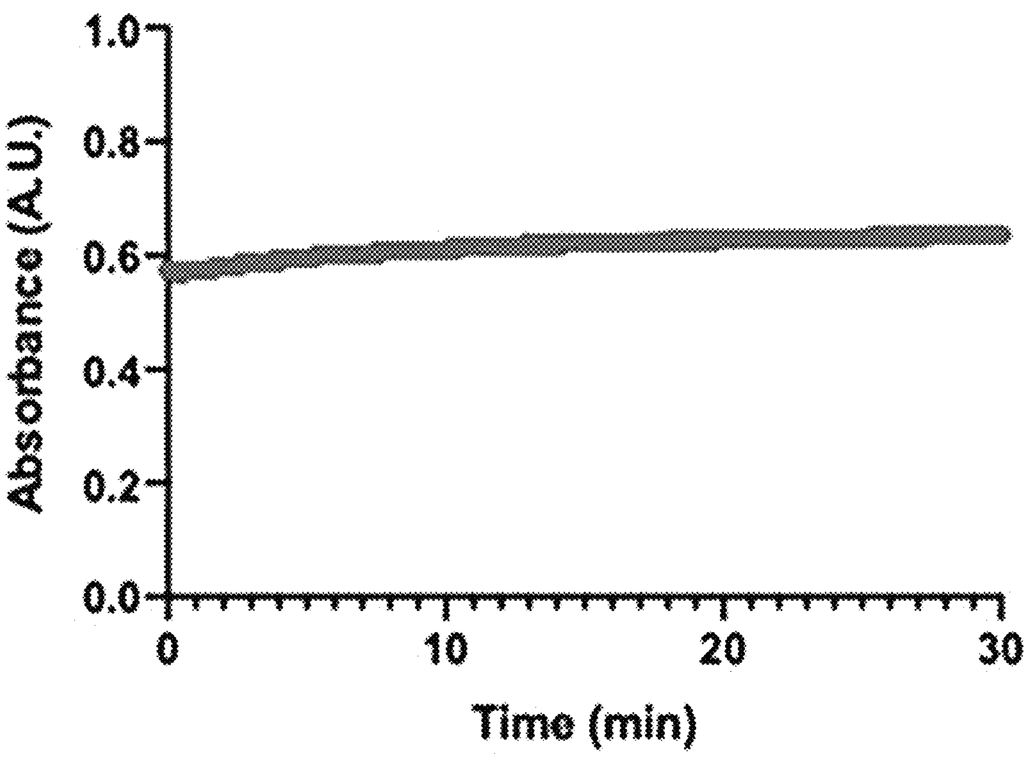

FIGS. 3A-3B show absorption studies depicting the stability of XanthCR-880 (20 μM) to the treatment of glutathione (10 mM) (FIG. 3A) and esterase (5 units) (FIG. 3B).

Figure 3C:
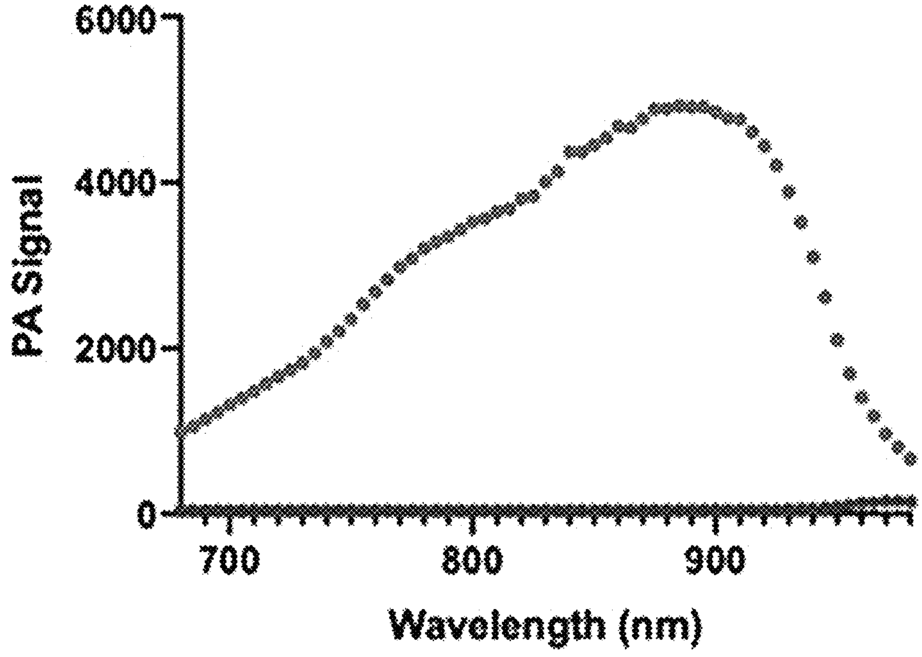

FIG. 3C shows a photoacoustic spectrum of XanthCR-880 (20 μM) in $CHCl_3$ (blue) and a vehicle control (red), λPA=890 nm.

Figure 3D:
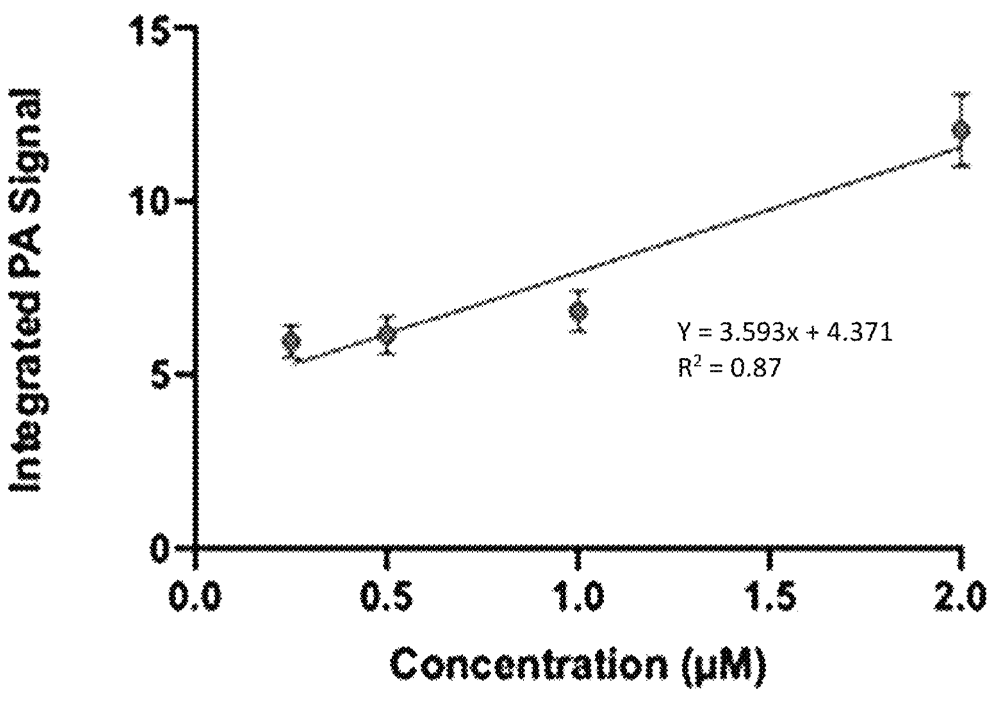

FIG. 3D shows the integrated photoacoustic signal of XanthCR-880 at 0.25 μm, 0.5 μm, 1.0 μm, and 2.0 μM in EtOH. The Limits Of Detection (LOD) was determined to be 0.36 μM according to the following equation (LOD=3×blank×SD of slope/$(1-\text{slope})^2$.

Figure 3E:
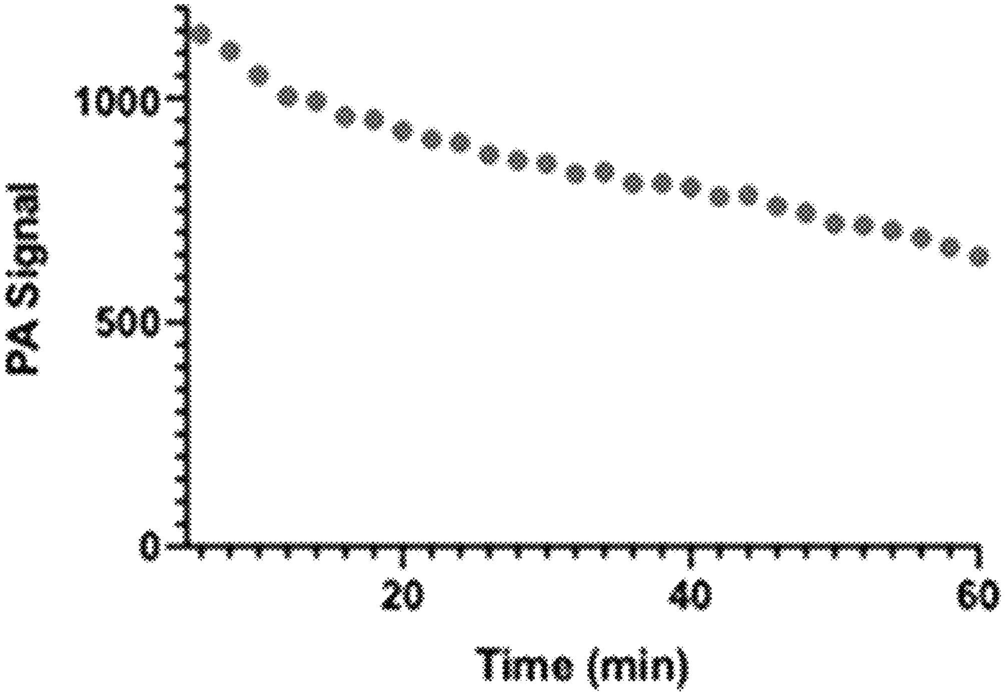

FIG. 3E shows the photobleaching of XanthCR-880 (20 μM) in $CHCl_3$ under continuous irradiation at 880 nm.

Figure 4:
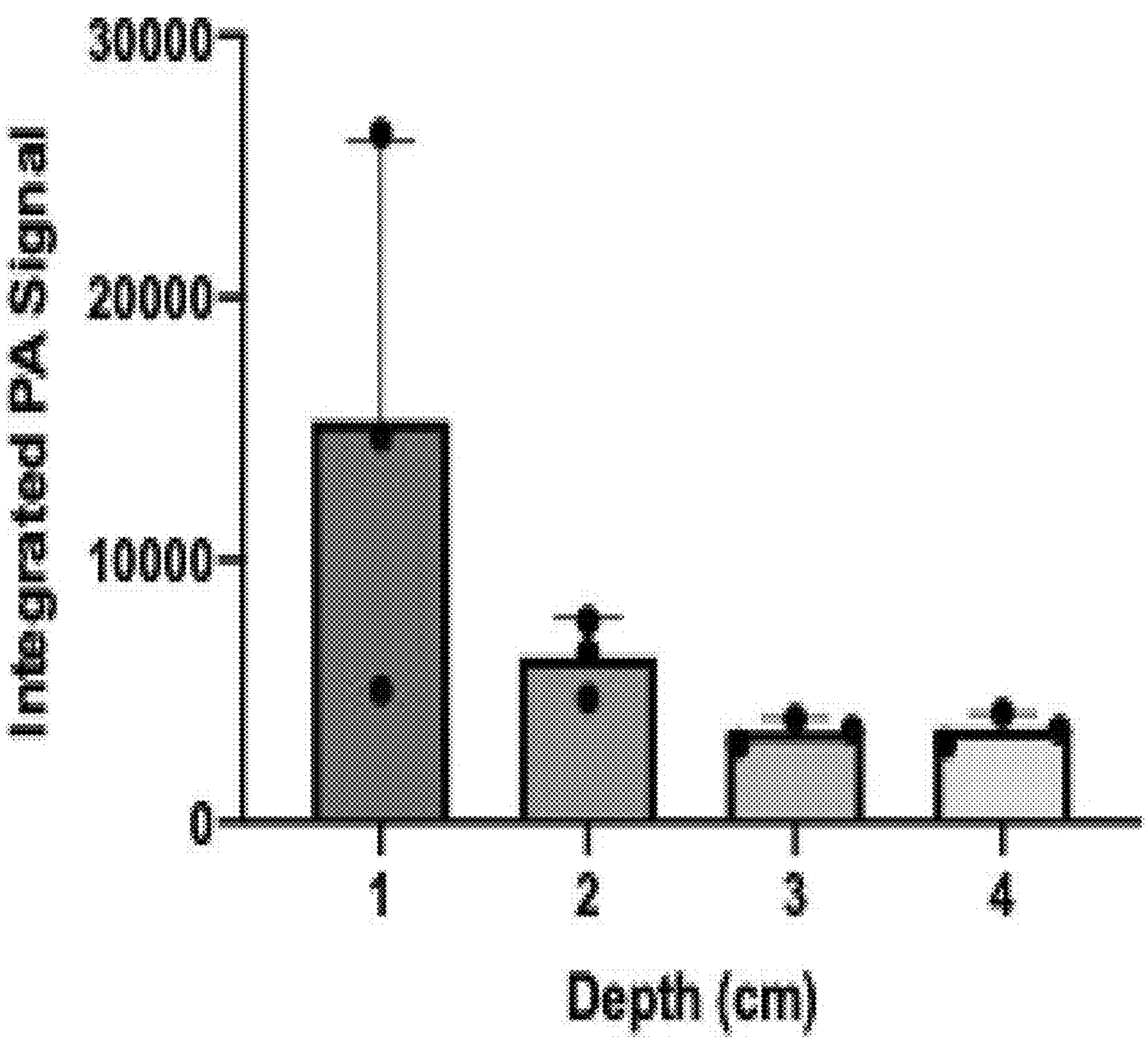
Figure 5A:
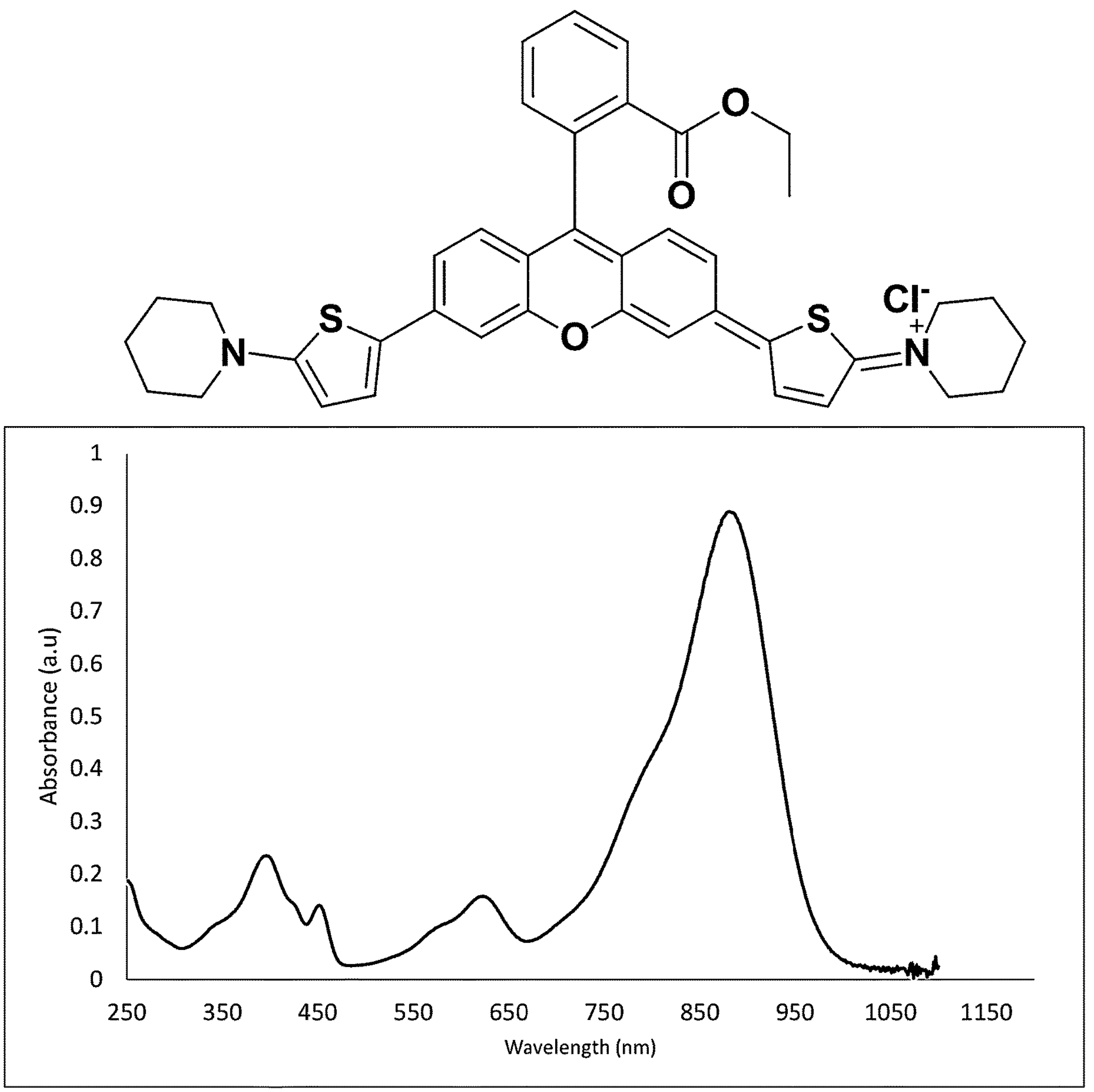
Figure 5B:
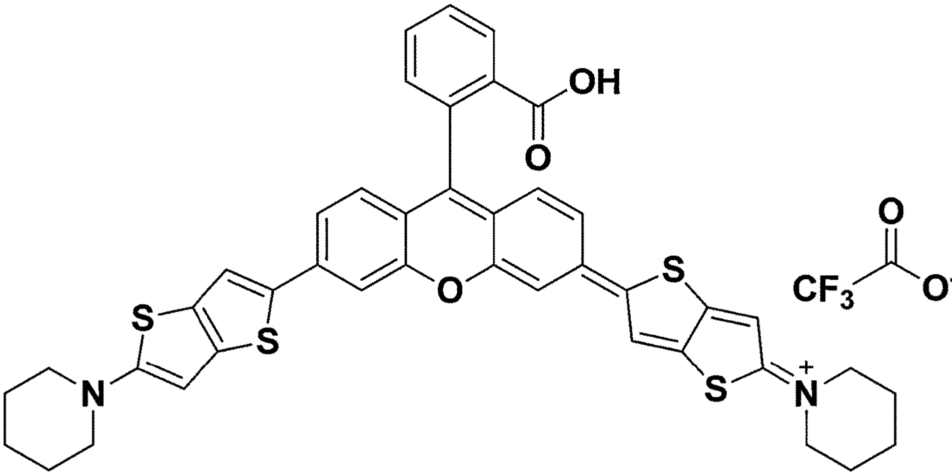
Figure 5B:
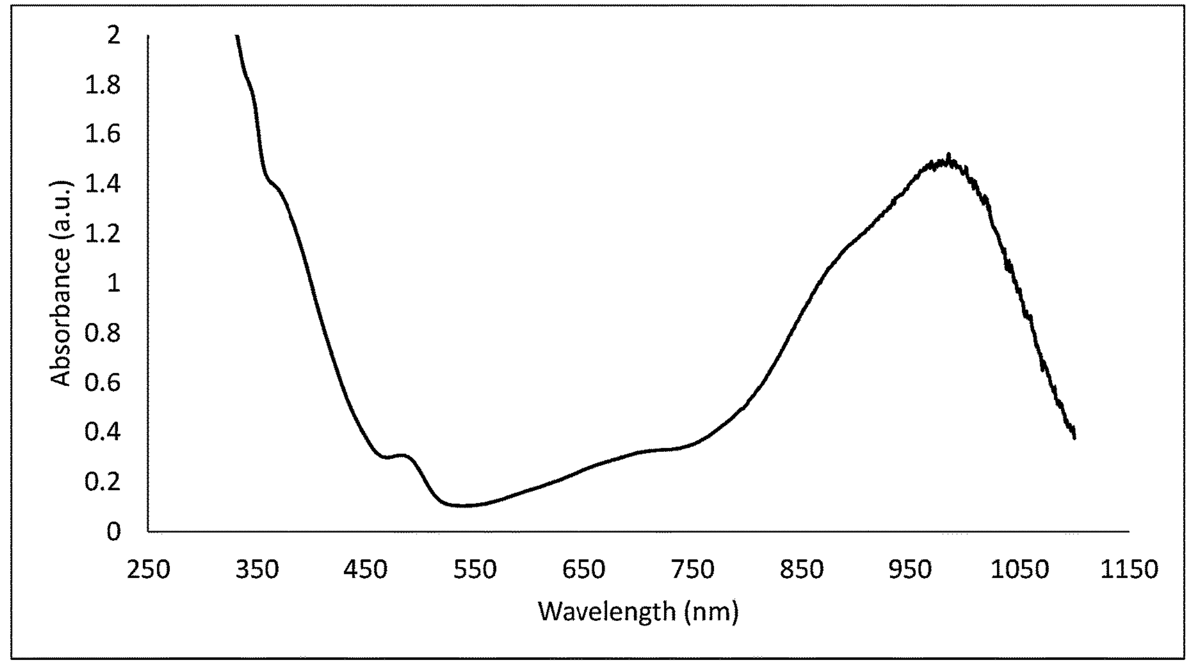
Figure 5C:
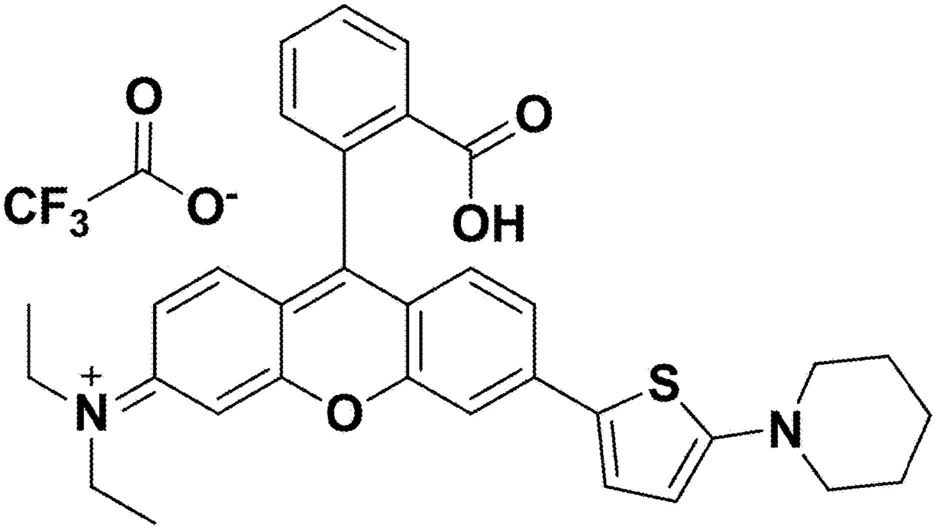
Figure 5C:
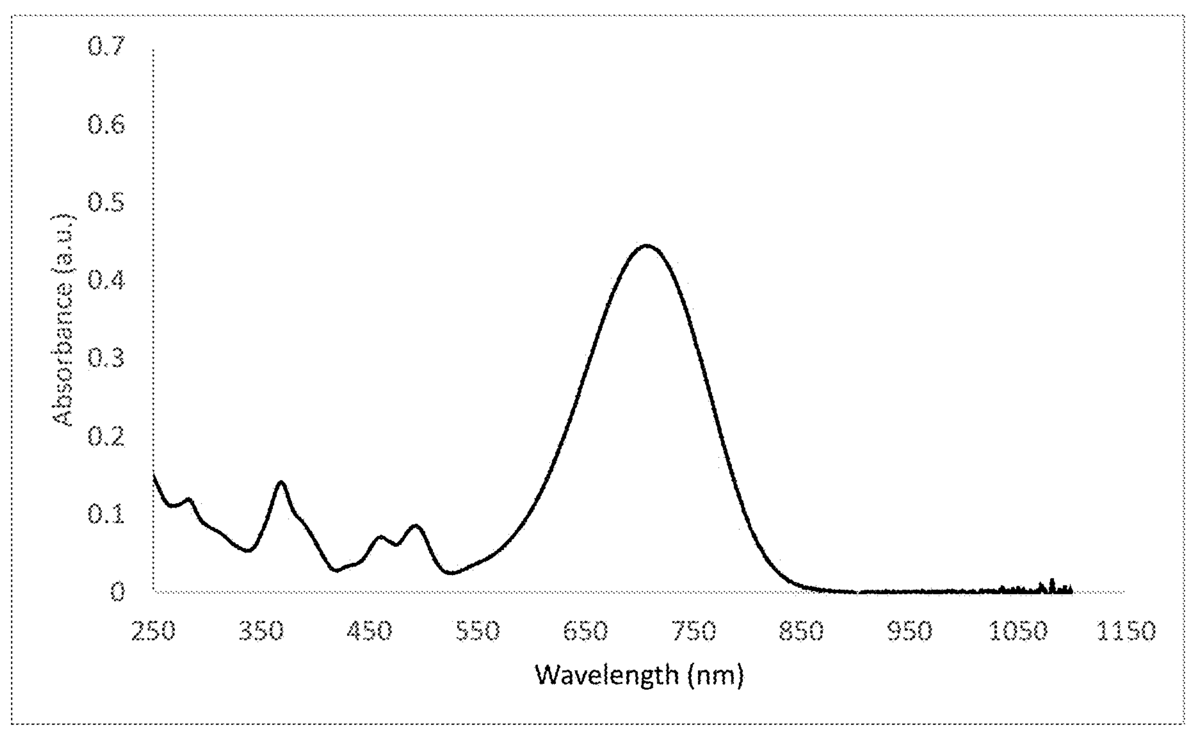
Figure 5D:
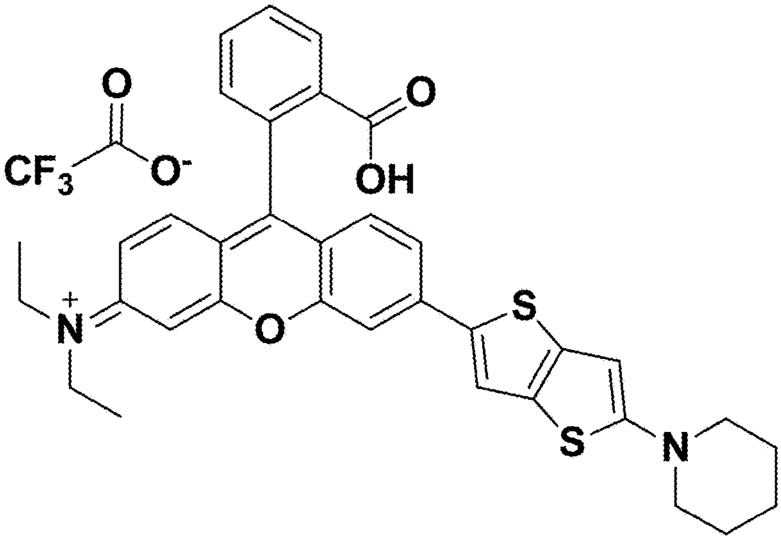
Figure 5D:
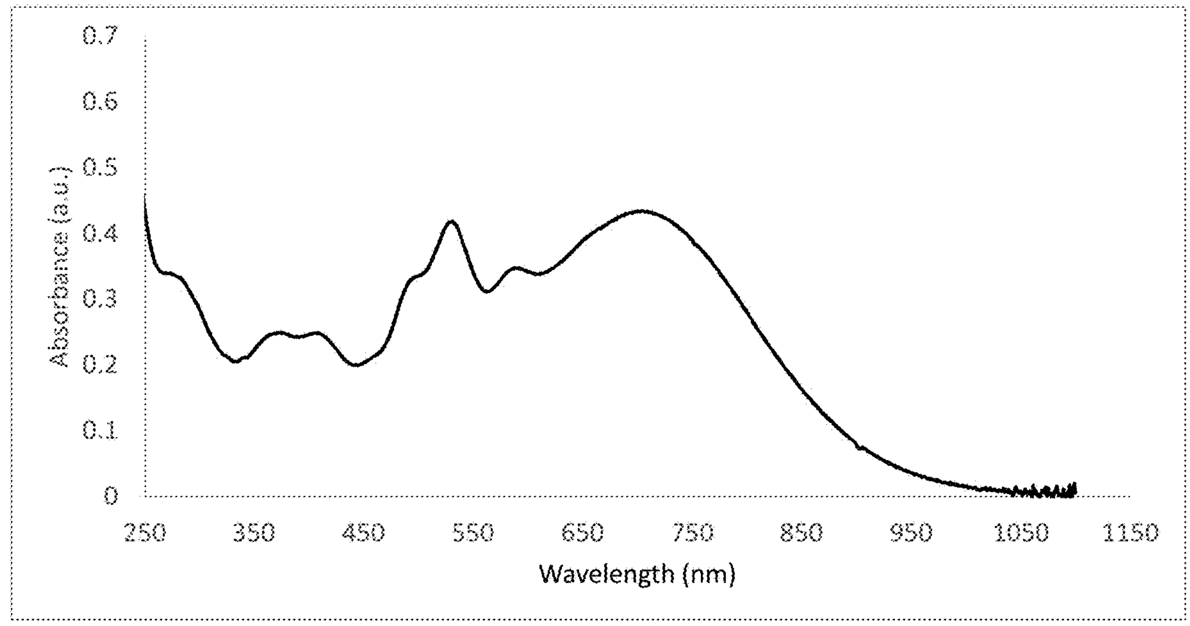
Figure 5E:
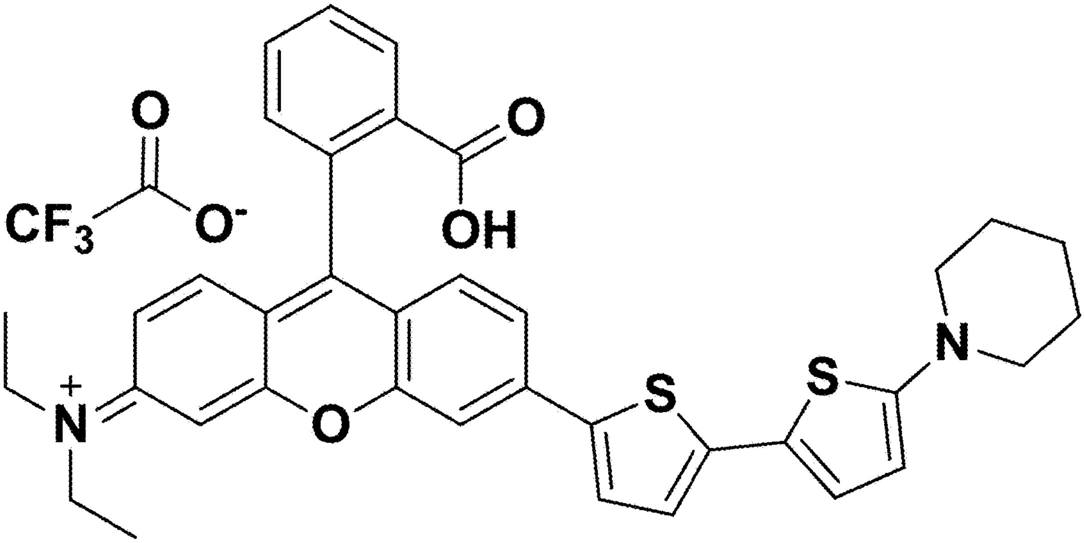
Figure 5E:
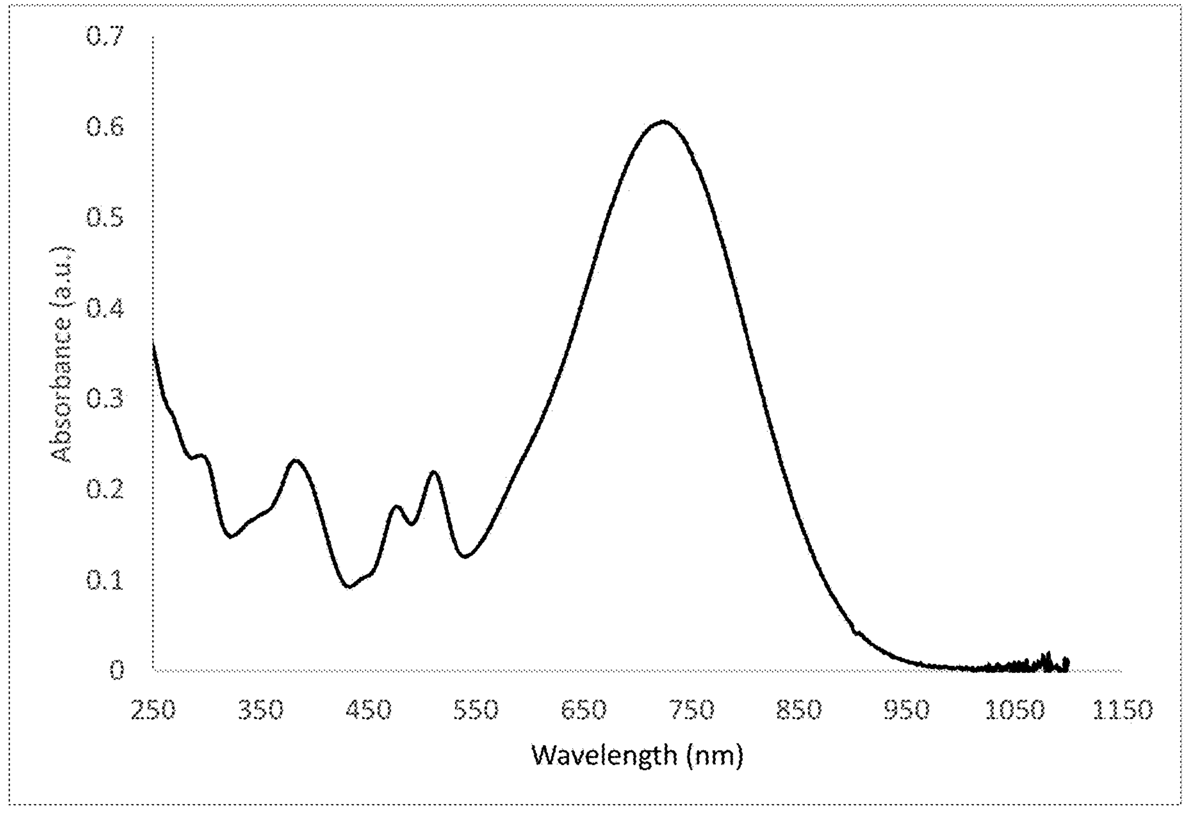

FIG. 4 shows an integrated photoacoustic signal of XanthCR-880 (20 μM) in phosphate buffered saline (PBS) with 0.1% SDS overlaid with swine tissue with a thickness of 1, 2, 3, or 4 cm.

FIGS. 5A, 5B, 5C, 5D, and 5E show the structure of NIR dyes of the disclosure and each of their respective IR absorbance spectra which show that the NIR dyes absorb light in the NIR II region.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

Small molecule organic dyes may be attractive for clinical applications because of their tendency to metabolize in the cells and their potential for low toxicity. Disclosed herein is a method for development of NIR organic dyes by combining donor and acceptor groups. In one aspect, the choice of a good donor-acceptor pair can significantly lower the optical bandgap of a dye due to the promotion of charge transfer events.

The novel NIR dyes can be used in biological imaging such as in vivo photoacoustic or fluorescence imaging of tumor angiogenesis monitoring, blood oxygenation mapping, functional brain imaging, skin melanoma detection, methemoglobin measuring, etc. In one aspect, the disclosure provides new materials that absorb light in the NIR I & II regions where biological tissues are most transparent. In a further aspect, the compositions allow for direct, real-time laser imaging of biological samples at a faster, more affordable rate than an MRI, while also potentially allowing real time analysis during surgery, as one example.

The xanthene-based dyes of the disclosure have outstanding photophysical properties and stimuli responses. For instance, the new NIR xanthene-based PA imaging agent XanthCR-880 shown in FIG. 1 has an absorption maximum at 880 nm that extends into the edge of the NIR-I region. The dye was used in PA studies, where it exhibited excellent photostability and a readily detectable PA signal at depths up to 4 cm in a tissue overlay application.

XanthCR-880 was developed using the donor-acceptor-donor (D-A-D) design. The design of the dye was based on two factors: (i) a good overlap of the thiophene donor and xanthene acceptor to lower the bandgap of the dye due to charge transfer events and (ii) an amino group connected to the thiophene to increase donor strength in the push-pull mechanism of xanthene-based dyes.

Donors

The xanthene dyes can be in a donor-acceptor (D-A) design or a donor-acceptor-donor (D-A-D) design. For the D-A-D design, the donors can be symmetrical or unsymmetrical. For symmetrical dyes, $R_1$ and $R_2$ are based on identical donors. For unsymmetrical dyes, $R_1$ and $R_2$ are not identical.

Although the structures described and drawn herein show the cationic charge on a single atom, the donors can be in resonance with one another such that the cationic charge can move from the donor at $R_1$ to the donor at $R_2$. $R_1$ and $R_2$ can be selected from one of the following Groups A, B and C:

Group A $R_1$ is hydrogen and $R_2$ is a donor which is a substituted or unsubstituted 1-(thiophen-2-yl)piperidine, 1-(thieno[3,2-b]thiophen-2-yl)piperidine or 1-([2,2'-bithiophen]-5-yl)piperidine; or Group B (Symmetrical Dyes)

Both $R_1$ and $R_2$ are the same donors and both are substituted or unsubstituted, and both are selected from 1-(thiophen-2-yl)piperidine, 1-(thieno[3,2-b]thiophen-2-yl)piperidine, and 1-([2,2'-bithiophen]-5-yl)piperidine; or Group C (Unsymmetrical Dyes)

$R_2$ is a different donor from $R_1$, and $R_1$ is a donor which is a substituted or unsubstituted 1-(thiophen-2-yl)piperidine, 1-(thieno[3,2-b]thiophen-2-yl)piperidine or 1-([2,2'-bithiophen]-5-yl)piperidine, and $R_2$ is a donor which is substituted or unsubstituted, and is selected from 1-(thiophen-2-yl)piperidine, 1-(thieno[3,2-b]thiophen-2-yl)piperidine, 1-([2,2'-bithiophen]-5-yl)piperidine, a $C_2$-$C_{12}$ dialkyl amine, indolizine derivative, diphenylamine, and julolidine.

In Group B, the dyes are symmetrical, such as XanthCR-880. In Group C, the dyes are unsymmetrical. For instance, the donor at $R_1$ could be 1-(thiophen-2-yl)piperidine and at $R_2$ could be 1-(thieno[3,2-b]thiophen-2-yl)piperidine; or both $R_1$ and $R_2$ can be 1-(thiophen-2-yl)piperidine but one is substituted and the other is not.

The preferred structure of the donors is shown below.

1-(thiophen-2-yl)piperidine

Nonionic structure

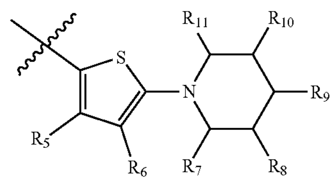

Ionic Structure

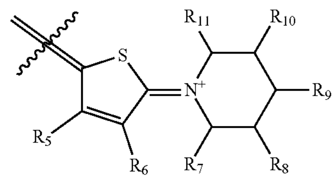

wherein $R_5$, $R_6$, $R_7$, $R_8$, $R_9$, $R_{10}$, and $R_{11}$ are each independently selected from hydrogen, sulfonate, halogen, hydroxy, amino, nitro, cyano, carboxy, an alkyl group having 1 to 20 carbons, alkenyl group having 2 to 20 carbon atoms, alkynyl group having 2 to 20 carbon atoms, an aryl group having 6 to 10 carbon atoms, a heterocyclic group having 3 to 16 carbon atoms, an alkoxy group having 1 to 20 carbon atoms, and an alkylether having 2-20 carbon atoms and 1 to 5 oxygen atoms; preferably the 1-(thiophen-2-yl)piperidine has 3 or fewer substituent, more preferably 1 substituent and most preferably no substituents, in other words, most preferably all of $R_5$, $R_6$, $R_7$, $R_8$, $R_9$, $R_{10}$, and $R_{11}$ are hydrogen.

The wavy line  is globally used herein to refer to the location of the bond between the donor and the xanthene core structure.

1-(Thieno[3,2-b]thiophen-2-yl)piperidine

Nonionic structure

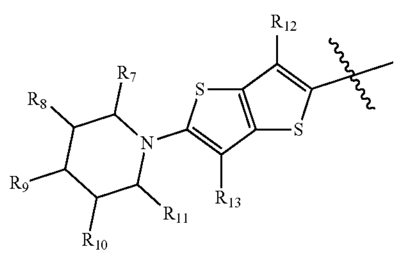

Ionic Structure

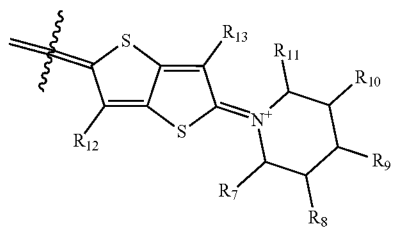

wherein $R_7$, $R_8$, $R_9$, $R_{10}$, and $R_{11}$ are as described above. $R_{12}$ and $R_{13}$ are each independently selected from hydrogen, sulfonate, halogen, hydroxy, amino, nitro, cyano, carboxy, an alkyl group having 1 to 20 carbon atoms, alkenyl group having 2 to 20 carbon atoms, alkynyl group having 2 to 20 carbon atoms, an aryl group having 6 to 10 carbon atoms, a heterocyclic group having 3 to 16 carbon atoms, an alkoxy group having 1 to 20 carbon atoms, and an alkylether having 2 to 20 carbon atoms and 1 to 5 oxygen atoms; preferably the 1-(thieno[3,2-b]thiophen-2-yl)piperidine has 3 or fewer substituents, more preferably 1 substituent and most preferably no substituents.

1-([2,2'-Bithiophen]-5-yl)piperidine

Nonionic structure

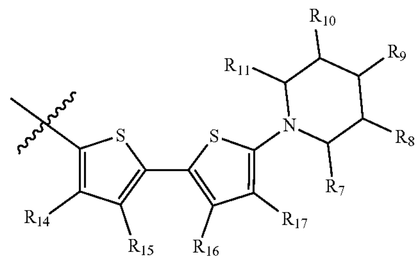

Ionic Structure

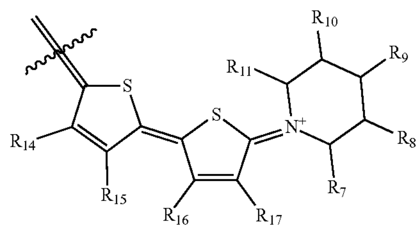

wherein $R_7$, $R_8$, $R_9$, $R_{10}$, and $R_{11}$ are as described above. $R_{14}$, $R_{15}$, $R_{16}$, and $R_{17}$ are each independently selected from hydrogen, sulfonate, halogen, hydroxy, amino, nitro, cyano, carboxy, an alkyl group having 1 to 20 carbon atoms, alkenyl group having 2 to 20 carbon atoms, alkynyl group having 2 to 20 carbon atoms, an aryl group having 6 to 10 carbon atoms, a heterocyclic group having 3 to 16 carbon atoms, an alkoxy group having 1 to 20 carbon atoms, and an alkylether having 2 to 20 carbon atoms and 1 to 5 oxygen atoms; preferably the 1-([2,2'-bithiophen]-5-yl)piperidine has 3 or fewer substituents, more preferably 1 substituent and most preferably no substituents.

$C_2$-$C_{12}$ Dialkyl Amine

A $C_2$-$C_{12}$ dialkyl amine which is bonded to the xanthene core at the amine nitrogen, and is optionally substituted with 1 to 3 substituents selected from an alkenyl group having 2 to 10 carbon atoms, alkynyl group having 2 to 10 carbon atoms, an alkoxy group having 1 to 20 carbon atoms, an alkylether having 2 to 20 carbon atoms and 1 to 5 oxygen atoms, an aryl group having 6 to 10 carbon atoms, and a heterocyclic group having 3 to 16 carbon atoms; preferably the $C_2$-$C_{12}$ dialkyl amine has 1 substituent and most preferably no substituents.

Indolizin-3-yl

Indolizin-3-yl which is bonded to the xanthene core at the 3-position, and is substituted or unsubstituted. Preferably, the indolizine-3-yl donor is substituted with 1 to 3 substituents which are independently selected from halogen, sulfonate, hydroxy, amino, nitro, cyano, carboxy, an alkyl group having 1 to 20 carbon atoms, alkenyl group having 2 to 20 carbon atoms, alkynyl group having 2 to 20 carbon atoms, an aryl group having 6 to 10 carbon atoms, a heterocyclic group having 3 to 16 carbon atoms, an alkoxy group having 1 to 20 carbon atoms, and an alkylether having 2 to 20 carbon atoms and 1 to 5 oxygen atoms; more preferably the indolizine-3-yl donor is substituted has 3 or fewer substituent; even more preferably the indolizine-3-yl donor is substituted at the 1- and 2-positions with an alkyl group having 1 to 5 carbons and an aryl group having 6 to 10 carbon atoms; and even more preferably, the indolizine- 3-yl donor is substituted at the 1-position with an alkyl group having 1 to 4 carbon atoms and at the 2-position with an aryl group having 6 to 8 carbon atoms; and most preferably, the indolizine donor is 1-methyl-2-phenylindolizin-3-yl.

Diphenylamine

The diphenylamine preferably has the following cationic structure (the corresponding nonionic structure is not shown):

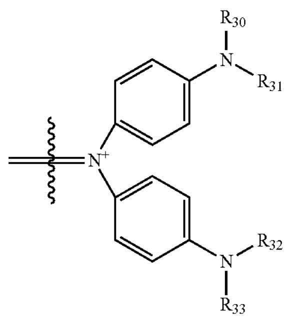

wherein $R_{30}$, $R_{31}$, $R_{32}$, and $R_{33}$ are independently selected from hydrogen, an alkyl group having 1 to 20 carbons, alkenyl group having 2 to 20 carbon atoms, alkynyl group having 2 to 20 carbon atoms, an alkoxy group having 1 to 20 carbon atoms, and an alkylether having 2 to 20 carbon atoms and 1 to 5 oxygen atoms, an aryl group having 6 to 10 carbon atoms, at least one combination of ($R_{30}$ and $R_{31}$) and ($R_{32}$ and $R_{33}$) together with N forming a substituted or unsubstituted pyrrolidine ring, a substituted or unsubstituted piperidine ring, a substituted or unsubstituted morpholine ring, a substituted or unsubstituted tetrahydropyridine ring or a substituted or unsubstituted cyclohexylamine ring.

Julolidine

Julolidine which preferably has the following cationic structure (the corresponding nonionic structure is not shown):

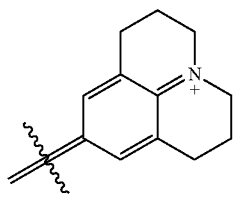

which is optionally substituted with 1 to 3 substituents independently selected from a halogen, sulfonate, hydroxy, amino, nitro, cyano, carboxy, an alkyl group having 1 to 20 carbon atoms, alkenyl group having 2 to 20 carbon atoms, alkynyl group having 2 to 20 carbon atoms, an alkoxy group having 1 to 20 carbon atoms, an alkylether having 2 to 20 carbon atoms and 1 to 5 oxygen atoms, an aryl group having 6 to 10 carbon atoms, and a heterocyclic group having 3 to 16 carbon atoms. Preferably, the julolidine donor is not substituted or has one substituent.

The wavy line 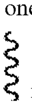 is globally used herein to refer to the location of the bond between the donor and the xanthene core structure.

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. It is noted that the dates of publication provided herein can be different from the actual publication dates, which can require independent confirmation.

Prior to describing the various aspects of the present disclosure, the following definitions are provided and should be used unless otherwise indicated. Additional terms may be defined elsewhere in the present disclosure.

Definitions

As used herein, “comprising” is to be interpreted as specifying the presence of the stated features, integers, steps, or components as referred to, but does not preclude the presence or addition of one or more features, integers, steps, or components, or groups thereof. Moreover, each of the terms “by”, “comprising,” “comprises”, “comprised of,” “including,” “includes,” “included,” “involving,” “involves,” “involved,” and “such as” are used in their open, non-limiting sense and may be used interchangeably. Further, the term “comprising” is intended to include examples and aspects encompassed by the terms “consisting essentially of” and “consisting of.” Similarly, the term “consisting essentially of” is intended to include examples encompassed by the term “consisting of. The transitional phrase “consisting essentially of” limits the scope of a claim to the specified materials or steps and those that do not materially affect the basic and novel characteristic(s) of the claimed invention.

As used in the specification and the appended claims, the singular forms “a,” “an” and “the” include plural referents unless the context clearly dictates otherwise. Thus, for example, reference to “a solvent,” “a linear alkyl group,” or “an alcohol,” include, but are not limited to, mixtures or combinations of two or more such solvents, linear alkyl groups, or alcohols, and the like.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as “about” that particular value in addition to the value itself. For example, if the value “10” is disclosed, then “about 10” is also disclosed. Ranges can be expressed herein as from “about” one particular value, and/or to “about” another particular value. Similarly, when values are expressed as approximations, by use of the antecedent “about,” it will be understood that the particular value forms a further aspect. For example, if the value “about 10” is disclosed, then “10” is also disclosed.

When a range is expressed, a further aspect includes from the one particular value and/or to the other particular value. For example, where the stated range includes one or both of the limits, ranges excluding either or both of those included limits are also included in the disclosure, e.g. the phrase “x to y” includes the range from ‘x’ to ‘y’ as well as the range greater than ‘x’ and less than ‘y’.

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of “about 0.1% to 5%” should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms “about,” “approximate,” “at or about,” and “substantially” mean that the amount or value in question can be the exact value or a value that provides equivalent results or effects as recited in the claims or taught herein. That is, it is understood that amounts, sizes, formulations, parameters, and other quantities and characteristics are not and need not be exact but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that “about” and “at or about” mean the nominal value indicated ±10% variation unless otherwise indicated or inferred. In general, an amount, size, formulation, parameter or other quantity or characteristic is “about,” “approximate,” or “at or about” whether or not expressly stated to be such. It is understood that where “about,” “approximate,” or “at or about” is used before a quantitative value, the parameter also includes the specific quantitative value itself, unless specifically stated otherwise.

As used herein, the term “effective amount” refers to an amount that is sufficient to achieve the desired modification of a physical property of the composition or material. For example, an “effective amount” of a NIR dye for imaging of a biological sample refers to an amount that is sufficient to achieve the desired image quality. The specific level in terms of wt % or mol % in a composition required as an effective amount will depend upon a variety of factors including the absorption maxima of the dye, whether the biological sample is an isolated sample or is part of an organism in vivo, the identity of any pharmaceutically acceptable carrier, and the capabilities of the device used to measure the photoacoustic signal produced by the dye via non-radiative decay.

As used herein, the term “donor’ refers to an electron donor and the term acceptor” refers to an electron acceptor in a donor-acceptor or donor-acceptor-donor dye. The terms “donor” and “acceptor” may be used to refer to the radicals in a donor-acceptor molecule (dye) or may he used to refer to separate chemical compounds that will form a donor-acceptor molecule once reacted together.

As used herein, the terms “optional” or “optionally” means that the subsequently described event or circumstance can or cannot occur, and that the description includes instances where said event or circumstance occurs and instances where it does not.

Unless otherwise specified, pressures referred to herein are based on atmospheric pressure (i.e. one atmosphere).

“NIR I” as used herein refers to the region of the electromagnetic spectrum having wavelengths from about 700 to about 900 nm, while “NIR II” refers to that region having wavelengths from about 900 nm to about 1700 nm. In one aspect, the compounds disclosed herein emit fluorescence and/or absorb radiation in the NIR II region.

As used herein, “fluorescence quantum yield” (Φ)) refers to the ratio of photons absorbed to photons emitted through fluorescence.

“Molar absorptivity,” “molar absorption coefficient,” and “extinction coefficient” refer to how strongly a chemical compound absorbs light at a given wavelength. Molar absorptivity is an intrinsic property of the compound; however, this coefficient varies with wavelength and solvent. Molar absorptivity is typically expressed in terms of absorption at a particular wavelength, such as the maximum position in the absorption band. Units are typically given as L/mol·cm or $M^{-1}\cdot cm^{-1}$. In one aspect, the disclosed NIR dyes have a high $\epsilon$ in the NIR II spectral region.

in one aspect, the NIR dye can have an absorption maximum in dimethyl sulfoxide (DMSO) at from about 800 nm to about 930 nm, or from about 830 nm, 840 nm, 850 nm, 860 nm, 870 nm, 880 nm, 890 nm or about 900 nm, or a combination of any of the foregoing values, or a range encompassing any of the foregoing values.

In another aspect, the NIR dye has a molar absorption coefficient of about 85,000 $M^{-1}\cdot cm^{-1}$ or greater, or of about 85,500 $M^{-1}\cdot cm^{-1}$, 86,000 $M^{-1}\cdot cm^{-1}$, 86,500 $M^{-1}\cdot cm^{-1}$, 87,000 $M^{-1}\cdot cm^{-1}$, 87,500 $M^{-1}\cdot cm^{-1}$, 88,000 $M^{-1}\cdot cm^{-1}$, 88,500 $M^{-1}\cdot cm^{-1}$, or about 88,900 $M^{-1}\cdot cm^{-1}$ or greater, or a combination of any of the foregoing values, or a range encompassing any of the foregoing values. In still another aspect, the NIR dye has a fluorescence quantum yield of less than 5%, or less than 4%.

Chemical Groups and Substituents

As used herein, the term “substituted” is contemplated to include all permissible substituents of organic compounds while not materially affecting the basic and novel characteristic(s) of the claimed invention. Also, the terms “substitution” or “substituted with” include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

The term "alkyl" as used herein is a linear, branched, or cyclic saturated hydrocarbon group of 1 to 20 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, and the like. The alkyl group can be cyclic (also referred to as "carbocyclic") or acyclic. The alkyl group can be branched or unbranched. The alkyl group can also be substituted or unsubstituted. For example, the alkyl group can be substituted with 1 to 3 substituents independently selected from a halogen, sulfonate, hydroxy, amino, nitro, cyano, carboxy, a heterocyclic group having 3 to 16 carbon atoms, an alkylether having 2 to 20 carbon atoms and 1 to 5 oxygen atoms, and an alkoxy group having 1 to 20 carbon atoms. A "lower alkyl" group is an alkyl group containing from one to six (e.g., from one to four) carbon atoms. The term alkyl group can also be a Ci alkyl, $C_1$-$C_2$ alkyl, $C_1$-$C_3$ alkyl, $C_1$-$C_4$ alkyl, Ci-05 alkyl, $C_1$-$C_6$ alkyl, $C_1$-$C_7$ alkyl, $C_1$-$C_8$ alkyl, $C_1$-$C_9$ alkyl, $C_1$-$C_{10}$ alkyl, and the like up to and including a $C_1$-$C_{18}$ alkyl.

The term "cycloalkyl" as used herein is a non-aromatic carbon-based ring composed of three carbon atoms to ten carbon atoms. Examples of cycloalkyl groups include, but are not limited to, cyclopropyl, cyclobutyl, cyclopentyl, cyclohexyl, norbornyl, and the like.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl, alkenyl or cycloalkyl as defined above.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, pyrene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, —$NH_2$, carboxylic acid, ester, ether, halide, hydroxy, ketone, azide, nitro, silyl, sulfo-oxo, or thiol as described herein.

The term "aldehyde" as used herein is represented by the formula —C(O)H. Throughout this specification "C(O)" is a short hand notation for a carbonyl group, i.e., C═O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein. A specific example of amino is —$NH_2$.

The term "carboxylic acid" as used herein is represented by the formula —C(O)OH.

The term "ester" as used herein is represented by the formula —$OC(O)A^1$ or —$C(O)OA^1$, where $A^1$ can be alkyl, cycloalkyl, alkenyl, cycloalkenyl, alkynyl, cycloalkynyl, aryl, or heteroaryl group as described herein.

The term "amide" as used herein is represented by the formula —$N(A^1)C(O)A^2$ or —$C(O)N(A^2)_2$, where $A^1$ and $A^2$ can be, independently, hydrogen, alkyl, cycloalkyl, alkenyl, cycloalkenyl, alkynyl, cycloalkynyl, aryl, or heteroaryl group as described herein.

The term "ether" as used herein is represented by the formula —$A^1OA^2$, where $A^1$ and $A^2$ can be, independently, an alkyl, cycloalkyl, alkenyl, cycloalkenyl, alkynyl, cycloalkynyl, aryl, or heteroaryl group described herein.

The terms "halo," "halogen" or "halide," as used herein can be used interchangeably and refer to F, Cl, Br, or I.

The term "heteroalkyl" as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. heteroalkyls can be substituted as defined above for alkyl groups.

The terms "heterocycle", "heterocyclic" or "heterocyclyl," as used herein can be used interchangeably and refer to single and multi-cyclic aromatic (heteroaromatic) or non-aromatic ring (heteroalkyl) systems in which at least one of the ring members is other than carbon. heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The heterocyclyl group can be a $C_2$ heterocyclyl, $C_2$-$C_3$ heterocyclyl, $C_2$-$C_4$ heterocyclyl, $C_2$-$C_6$ heterocyclyl, $C_2$-$C_6$ heterocyclyl, $C_2$-$C_7$ heterocyclyl, $C_2$-$C_8$ heterocyclyl, $C_2$-$C_9$ heterocyclyl, $C_2$-$C_{10}$ heterocyclyl, $C_2$-$C_{11}$ heterocyclyl, and the like up to and including a $C_2$-$C_{18}$ heterocyclyl. For example, a $C_2$heterocyclyl comprises a group which has two carbon atoms and at least one heteroatom, including, but not limited to, aziridinyl, diazetidinyl, dihydrodiazetyl, oxiranyl, thiiranyl, and the like. Alternatively, for example, a Cs heterocyclyl comprises a group which has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

The term "hydroxyl" or "hydroxy" as used herein is represented by the formula —OH.

The term "nitro" as used herein is represented by the formula —$NO_2$.

The term "nitrile" or "cyano" as used herein is represented by the formula —CN.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position.

Combinations of substituents envisioned by this invention are preferably those that result in the formation of stable or chemically feasible compounds. It is also contemplated that, in certain aspects, unless expressly indicated to the contrary, individual substituents can be further optionally substituted (i.e., further substituted or unsubstituted).

The term "radical," which as used in the specification and concluding claims, refers to a fragment, group, or substructure of a molecule described herein, regardless of how the molecule is prepared. For example, a 2,4-thiazolidinedione radical in a particular compound has the structure:

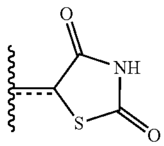

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

Pharmaceutically Acceptable Carriers and Biocompatibility

In various aspects, the dyes of the present disclosure can be given to a patient in a biocompatible composition in an amount effective to allow for PA or Fl analysis of a particular tissue, organ or system. As used herein, "biocompatible" refers to a material or composition that does not cause harm to living tissue. In one aspect, the MR dyes disclosed herein are biocompatible. Herein, the term "biocompatible" is used interchangeably with "pharmaceutical" or "pharmaceutically acceptable". As used herein, "pharmaceutically acceptable carriers" means one or more of a pharmaceutically acceptable diluents, preservatives, antioxidants, solubilizers, emulsifiers, coloring agents, releasing agents, coating agents, sweetening, flavoring and perfuming agents, and adjuvants.

In another aspect, the present disclosure relates to pharmaceutical compositions include those suitable for parenteral administration, such as intravenous administration, although the most suitable route in any given case will depend on the particular host, and nature and severity of the conditions for which the NIR dyes ingredient are being administered.

In various aspects, the present disclosure also relates to a pharmaceutical composition comprising, a pharmaceutically acceptable carrier or diluent and an effective amount of the MR dye compounds of the present disclosure for bioimaging, a product of the method of making thereof, a pharmaceutically acceptable salt thereof, a hydrate thereof, a solvate thereof, a polymorph thereof, or a stereochemically isomeric form thereof. In a further aspect, the compounds of the present disclosure, a product of the method of snaking thereof, a pharmaceutically acceptable salt thereof, a hydrate thereof, a solvate thereof, a polymorph thereof, or a stereochemically isomeric form thereof, or any subgroup or combination thereof may be formulated into various pharmaceutical forms for administration purposes.

Pharmaceutical compositions of the present disclosure suitable for parenteral administration can include sterile aqueous or oleaginous solutions, suspensions, or dispersions. Furthermore, the compositions can be in the form of sterile powders for the extemporaneous preparation of such sterile injectable solutions or dispersions. In some aspects, the final injectable form is sterile and must be effectively fluid for use in a syringe. The pharmaceutical compositions should be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Injectable solutions, for example, can be prepared in which the carrier comprises saline solution, such as a HEPES Buffered Saline or similar solutions.

As used herein, "nontoxic" refers to a material or composition that does not kill cells or organisms. In a further aspect, the NIR dyes disclosed herein are nontoxic.

Absorbance and Fluorescence of NIR Dyes

In terms of brightness, luminosity is dependent on the fluorophores' extinction coefficient (molar absorptivity) or ability to absorb light, and its quantum efficiency or effectiveness at transforming absorbed light into emitting luminescence. The NIR dyes themselves are not very fluorescent, but they are sufficiently fluorescent for brightness imaging. For instance, when the NIR dye binds to proteins, the protein becomes more easily detectable.

Methods for Making NIR Dyes n an aspect, the disclosure relates to a method for making a NIR dyes, the method comprising:

(a) Performing a C-H arylation reaction by combining a Donor and an Acceptor of Formula II with a catalyst in a solvent to form a reaction mixture, Formula II

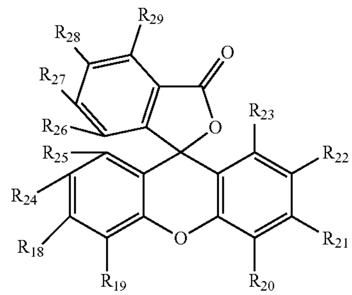

wherein $R_{18}$ and $R_{21}$ are individually selected from Cl, Br, I and $OSO_2R_{52}$ wherein $R_{52}$ is a hydrogen or lower alkyl;

wherein $R_{19}$, $R_{20}$, $R_{22}$, $R_{23}$, $R_{24}$, $R_{25}$, $R_{26}$, $R_{27}$, $R_{28}$, and $R_{29}$ are each independently selected from hydrogen or an alkyl group having 1 to 20 carbon atoms, or wherein one or more pair of $R_{22}$ and $R_{23}$, $R_{24}$ and $R_{25}$, $R_{25}$ and $R_{26}$, $R_{26}$ and $R_{27}$, $R_{27}$ and $R_{28}$, $R_{28}$ and $R_{29}$, together with the carbons they are attached form a saturated or unsaturated 6 membered ring; and wherein the Donor(s) is substituted or unsubstituted and comprises: (X) 1-(thiophen-2-yl)piperidine, 1-(thieno[3,2-b]thiophen-2-yl)piperidine or 1-([2,2'-bithiophen]-5-yl)piperidine; and (Y) 1-(thiophen-2-yl)piperidine, 1-(thieno[3,2-b]thiophen-2-yl)piperidine, 1-([2,2'-bithiophen]-5-yl)piperidine, $C_2$-$C_{12}$ dialkyl amine, indolizine, diphenylamine, and julolidine, to thereby replace the groups at $R_{18}$ and $R_{21}$ with said Donor(s);

(b) a ring opening reaction by transesterification with an alcohol to give the NIR dye of formula I Formula I

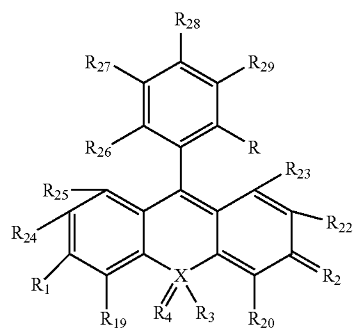

wherein X is O, $R_3$ and $R_4$ are absent;

R is selected from —C(O)OH or an ester group represented by the formula —C(O)OA[1], wherein $A^1$ is a linear or branched $C_1$-$C_{18}$ alkyl group;

wherein $R_{19}$, $R_{20}$, $R_{22}$, $R_{23}$, $R_{24}$, $R_{25}$, $R_{26}$, $R_{27}$, $R_{28}$, and $R_{29}$ are as described above; and $R_1$ and $R_2$ are both selected from one of the following Groups B and C:

Group B

Both $R_1$ and $R_2$ are the same donors and both are substituted or unsubstituted, and are selected from 1-(thiophen-2-yl)piperidine group, 1-(thieno[3,2-b]thiophen-2-yl)piperidine, and 1-([2,2'-bithiophen]-5-yl)piperidine; or Group C $R_1$ and $R_2$ are different donors and $R_1$ is a donor which is substituted or unsubstituted and is a 1-(thiophen-2-yl)piperidine, 1-(thieno[3,2-b]thiophen-2-yl)piperidine or 1-([2,2'-bithiophen]-5-yl)piperidine and $R_2$ is a donor which is substituted or unsubstituted and is selected from 1-(thiophen-2-yl)piperidine, 1-(thieno[3,2-b]thiophen-2-yl)piperidine, 1-([2,2'-bithiophen]-5-yl)piperidine, $C_2$-$C_{12}$ dialkyl amino, indolizine-3-yl, diphenylamino, and julolidinyl. In Group C, the dyes are unsymmetrical. For instance, the donor at $R_1$ could be 1-(thiophen-2-yl)piperidine and at $R_2$ could be 1-(thieno[3,2-b]thiophen-2-yl)piperidine; or both $R_1$ and $R_2$ can be 1-(thiophen-2-yl)piperidine but one is substituted and the other is not.

Preferably, the compound formed in step (a) has the following structure:

3

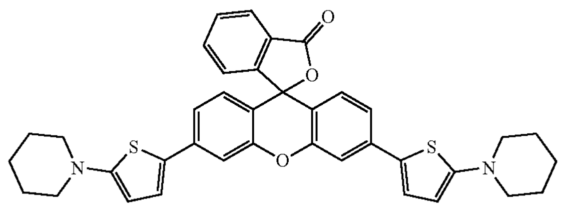

In one aspect, the solvent in step (a) can be selected from N-methyl-2-pyrrolidone (NMP), N,N-dimethylacetamide (DMA), dimethylformamide (DMF), toluene, tetrahydrofuran (TRF), dioxane, or any combination thereof.

In one aspect, in step (a), the reaction mixture can be heated at a temperature from about 80° C. to about 150° C., or at about 80° C., 85° C., 90° C., 95° C., 100° C., 105° C., 110° C., 115° C., 120° C., 125° C., 130° C., 135° C., 140° C., 145° C., or about 150° C., or a combination of any of the foregoing values, or a range encompassing any of the foregoing values. In another aspect, the reaction mixture can be heated for from about 6 hours to about 30 hours, or for about 6 hours, 6.5 hours, 7 hours, 7.5 hours, 8 hours, 8.5 hours, 9 hours, 9.5 hours, 10 hours, 11 hours, 12 hours, 13 hours, 14 hours, 15 hours, 16 hours, 17 hours, 18 hours, 19 hours, 20 hours, 21 hours, 22 hours, 23 hours, or about 24 hours, or a combination of any of the foregoing values, or a range encompassing any of the foregoing values. In one aspect, step (a) can be conducted in an inert atmosphere such as, for example, nitrogen.

In one aspect, step (a) further includes admixing a catalyst with the compound of Formula II and the Donor. The catalyst can be Bis(triphenylphosphine)palladium(II) dichloride ($PdCl_2(PPh_3)_2$), Palladium(II)acetate ($Pd(OAc)_2$), Tris(dibenzylideneacetone)dipalladium(0) ($Pd(dba)_3$)·$CHCl_3$, or any combination thereof. In a further aspect, from about 0.01 to about 0.1 moles of catalyst can be used per mole of compound of Formula II. Further in this aspect, about 0.01, 0.02, 0.03, 0.04 or about 0.05 moles of catalyst can be used, or a combination of any of the foregoing values, or a range encompassing any of the foregoing values.

In another aspect, step (a) further includes admixing a base with the compound of Formula II and the Donor. In still another aspect, the base can be potassium acetate (KOAc), sodium acetate (NaOAc), $Cs_2CO_3$, $KO^tBu$, $NaO^tBu$, $K_2CO_3$, $Na_2CO_3$, or any combination thereof. In one aspect, from about 2.0 moles to about 6.0 moles of base can be used per mole of compound of Formula II. Further in this aspect, about 2.0, 2.7, 3.0, 3.2, or about 3.3 moles to about 6.0, 5.5, 5.0, or about 4.5 moles of base can be used, or a combination of any of the foregoing values, or a range encompassing any of the foregoing values.

In still another aspect, step (a) further includes admixing a ligand with the compound of Formula II and the Donor compound. In a further aspect, the ligand can be triphenylphosphine ($PPh_3$), Dicyclohexyl[2',4',6'-tris(propan-2-yl)[1,1'-biphenyl]-2-yl]phosphane (Xphos), 2,2'-bis(diphenylphosphino)-1-1'-binaphthyl (BINAP), $(^tBu)_2PMeHBF_4$, or any combination thereof. In an aspect, from about 1 to about 4 moles of ligand can be used per mole of catalyst, or about 1.5 to about 2.5, or about 2 moles of ligand per mole of catalyst can be used, or a combination of any of the foregoing values, or a range encompassing any of the foregoing values.

In an aspect, in step (b), the alcohol used in the transesterification reaction is also a solvent or cosolvent. In an aspect, the alcohol is methanol, ethanol, propanol, isopropanol, or butyl alcohol. In an aspect, the reaction mixture is heated to reflux. In another aspect, the reaction mixture can be heated for from about 6 hours to about 24 hours, or for about 6, 6.5, 7, 7.5, 8, 8.5, 9, 9.5, 10, 11, 12, 13, 14, 15, 16, 17, 18, 19, 20, 21, 22, 23, or about 24 hours, or a combination of any of the foregoing values, or a range encompassing any of the foregoing values. In one aspect, step (b) can be conducted in an inert atmosphere such as, for example, nitrogen.

As noted above, the donors can be symmetrical or unsymmetrical in a D-A-D designed molecule. For symmetrical dyes, such as XanthCR-880, the donor is combined with the acceptor using twice the moles of the donor when compared to the moles of acceptor. On the other hand, an NIR dye having an unsymmetrical D1-A-D2 design could be prepared by essentially the same synthesis except that some of the D1 reactants are replaced with D2 reactants, such that:

total moles (D1+D2) is twice the moles of A. In addition, NIR dyes having $R_1$=H could be made by starting with an acceptor having only one leaving group and using equal moles of acceptor and donor.

Also disclosed are NIR dyes produced by the disclosed methods.

Compositions, Methods, and Devices Using the NIR Dyes

In one aspect, disclosed herein is a composition including an NIR dye disclosed herein which optionally has a carrier. In a further aspect, the carrier can be a pharmaceutically-acceptable carrier. in still another aspect, the compositions can be biocompatible and/or nontoxic.

Also disclosed herein are methods for imaging a biological sample. In one aspect, the method includes the steps of (a) contacting the biological sample with a disclosed composition; (b) exposing the biological sample and the composition to NIR radiation; and (c) observing PA emission in the biological sample. In a further aspect, the biological sample includes an organelle, a cell, a tissue, an organ, or any combination thereof.

Other potential applications include composites comprising the dyes in a polymer matrix for commodity items such as eye glasses, night vision glasses or smart glasses, sensors, laser, and optoelectronic materials for electrical devices.

Now having described the aspects a the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

EXAMPLES

The following examples are put forth so as to provide those of ordinary skill in the art with a complete disclosure and description of how the compounds, compositions, articles, devices and/or methods claimed herein are made and evaluated and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in 20° C.-22° C. or is at ambient temperature; and pressure is at or near atmospheric.

All chemicals and solvents were purchased from commercial suppliers and used without further purification unless other-wise specified. $^1$H NMR (500 MHz) and $^{13}$C NMR (500 MHz) spectra were recorded in deuterated solvents on a Bruker ADVANCE 500 NMR Spectrometer. J values are expressed in Hz and quoted chemical shifts are in ppm downfield from tetramethylsilane (TMS) reference using the residual protonated solvents as an internal standard. The signals have been designated as follows: s (singlet), d (doublet), t (triplet), m (multiplets). All the $^{13}$C NMR are proton decoupled. High resolution mass spectra (HRMS) were determined on Broker-micrOTOF-Q II Mass Spectrometer. Concentrations are given in μM. Absorption spectra were acquired using a Cary 5000 UV-Vis-NIR spectrophotometer in a 1 cm quartz cell.

Fluorescence spectra were acquired using a custom-built setup with discrete excitation wavelengths ranging from 226 nm to 1059 nm with a temperature range from 4.2 K to 300 K using a liquid He bath cryostat. Alternatively, a Horiba QuantaMaster 8075-21 spectrofluorometer with xenon lamp excitation and liquid nitrogen cooled indium gallium arsenide solid state detector could be used. 882 mu excitation was chosen to coincide with a Xe emission peak.

Photoacoustic A imaging was performed on an iThera Medical MSOT inVision 128 tomographer.

Example 1: Synthesis of XanthCR-880 (1-{5-[(3E)-9-[2-(Ethoxycarbonyl)phenyl]-6-[5-(piperidin-1-yl)thiophen-2-yl]-3H-xanthen-3-ylidene]-2,5-dihydrothiophen-2-ylidene}-1λ5-piperidin-1-ylium chloride)

As shown in FIG. 1, the XanthCR-880 dye was prepared from inexpensive commercially available materials in three simple steps that did not require tedious purification methods. The synthesis began with the coupling of 2-bromothiophene and piperidine using a copper catalyst to give Compound 1 of FIG. 1 in 71% yield. Initially, Compound 1 was subjected to the direct C—H arylation reaction with 3,6-dibromofluoran (Compound 2 of FIG. 1) to give Compound 3 of FIG. 1 in 63% yield. Compound 1 (335.0 mg, 2 mmol), Compound 2 (458.1 mg, 1 mmol), dimethylformamide (DMF) (2.3 mL), $Pd(OAc)_2$ (5 mol %), $PPh_3$ (10 mol %), and KOAc (324.0 mg, 3.3 mmol) were placed in a microwave vial that was flushed with nitrogen and sealed. The vial and its contents were heated at 130° C. in an oil bath for 24 h. The reaction was monitored by TLC (silica plates) and 1H NMR. Once it was determined that the reaction conversion had plateaued, the crude was diluted with 50 mL of dichloromethane (DCM) and washed with water (3×50 mL). The crude product was dried over anhydrous sodium sulfate, filtered, and concentrated under reduced pressure. The crude product was purified by column chromatography on silica gel (hexanes:ethyl acetate v/v 70:30) to give the 400 mg of Compound (3) as a yellow solid in 63% yield. Compound (3) was characterized by $^1$H and $^{13}$C NMR spectroscopy. $^1$H NMR (500 MHz, $CDCl_3$): δ (ppm) 8.03 (d, J=7.5 Hz, 1H), 7.64 (dt, J=23.8, 7.2 Hz, 2H), 7.35 (d, J=1.6 Hz, 2H), 7.19 (d, J=7.5 Hz, 1H), 7.12 (dd, J=8.3, 1.7 Hz, 2H), 7.09 (d, J=4.0 Hz, 2H), 6.72 (d, J=8.3 Hz, 2H), 6.04 (d, J=4.0 Hz, 2H), 3.21 - 3.16 (m, 8H), 1.75-1.70 (m, 8H), 1.6 -1.56 (m, 4H). $^{13}$C {1H} NMR (126 MHz, $CDCl_3$): δ (ppm) 169.7, 160.7, 153.5, 151.8, 137.9, 135.2, 129.8, 128.5, 127.2, 126.7, 125.2, 124.1, 120.0, 115.8, 112.0, 105.1, 83.0, 52.2, 25.3, 23.9. HRMS (ESI) m/z: [M+Na]+Calcd for C38H34N2O3S2 653.1903; found 653.1907.

Treatment of Compound (3) with TFA resulted in the opened form; however, to maintain the ring-opened form, Compound (3) was esterified with ethanol to give XanthCR-880 in 62% yield. Compound (3) (385.0 mg, 0.6 mmol) was transferred to a 250 mL two-neck round bottom flask and flushed with nitrogen for 10 min. 1,2-dichloroethane (12 mL) and $POCl_3$ (1.68 mL) were added to the flask and the reaction was refluxed in an oil bath for 24 h. The reaction mixture was cooled to room temperature and concentrated under reduced pressure to give a green solid, which was used in the next step without further purification. The reaction mixture was thoroughly flushed with nitrogen for 10 min, followed by the addition of dry ethanol (10 mL) and refluxed in an oil bath for 24 h. The reaction mixture was concentrated under reduced pressure and the crude product was purified by column chromatography on silica gel (DCM: ethanol v/v 90:10) to give a green solid. The solid was dissolved in DCM (50 mL), washed with brine (3×100 mL) and 2.0 M HCl solution (3×100 mL), and dried over sodium sulfate, filtered, and concentrated under reduced pressure to give 250 mg of XanthCR-880 as a green solid in 62% overall yield. $^{1}H$ NMR (500 MHz, $CDCl_3$): δ (ppm) 8.32 (d, J=7.6 Hz, 1H), 7.82 (s, 3H), 7.75 (t, J=7.4 Hz, 1H), 7.50 (d, J=8.6 Hz, 2H), 7.41 — 7.31 (m, 3H), 6.98 (d, J=8.6 Hz, 2H), 6.39 (s, 2H), 4.07 (dd, J=13.4, 6.6 Hz, 2H), 3.49 (s, 8H), 1.82 — 1.68 (m, 12H), 1.07 (t, J=6.7 Hz, 3H). $^{13}C$ {1H} NMR (126 MHz, $CDCl_3$): δ (ppm) 167.4, 165.3, 156.4, 156.1, 145.5, 135.5, 133.8, 133.4, 131.8, 130.7, 129.2, 125.1, 123.9, 121.2, 109.0, 107.6, 61.9, 52.2, 25.5, 23.8, 14.1. HRMS (ESI) m/z: [M]+ Calcd for C40H39N2O3S2+659.2396; found 659.2393.

The closed (Compound 3) and opened (XanthCR-880) forms of the dye can be differentiated by the shift in the resonance for the proton ortho to the carbonyl group on the spirolactone moiety using $^{1}H$ NMR; this proton's peak shifts downfield (~8.32 ppm) in the opened form compared to the closed form (~8.03 ppm). Additionally, the chemical shift of the C-9 carbon is different between the open and closed forms.

The IR spectrums of the closed (Compound 3) and opened (XanthCR-880) forms of the dye are very distinct. The IR spectrums were obtained in dichloromethane (DCM) and dimethyl sulfoxide (DMSO) (FIG. 2). The maximum absorption wavelength ($\lambda_{abs}$) of the closed form (Compound 3) is 372 nm. However, when the dye was trapped in the opened form as the ethyl ester (XanthCR-880), the $\lambda_{abs}$ shifted to 880 nm in DCM and 890 nm in DMSO, both of which are at the edge of the NIR I region and trail into the NIR II region.

Attempts to determine the fluorescent quantum yield showed that XanthCR-880 had sufficient fluorescence for brightness imaging.

The XanthCR-880 dye was also shown to have excellent stability. The stability of XanthCR-880 dye was tested against glutathione, which is a potential reducing agent in biological media. The XanthCR-880 dye (17 μM) was prepared in 40% DMSO/60% PBS solution with 10 mM reduced glutathione and evaluated the change in the maximum absorption at 880 nm. The 10 mM concentration of reduced glutathione was selected to reflect the highest reported levels found in the body (i.e., liver). There was no change observed in the absorbance of the dye after 30 min. See FIG. 3A. These results suggest that the dye is stable to glutathione under the conditions and may be resistant to metabolic degradation by thiols in areas where glutathione levels are the highest.

Furthermore, the stability of XanthCR-880 was evaluated in the presence of esterases, which can potentially hydrolyze the ethyl ester, resulting in the closed PA-inactive form (Compound 3). When XanthCR-880 was incubated at room temperature for 30 min with porcine liver esterase, no significant change in the absorbance was noted (FIG. 3B). The XanthCR-880 dye was evaluated for its compatibility as a PA contrast agent in chloroform (FIG. 3C) and PBS buffer and observed that the strongest intensity (XPA) was at 890 nm and 865 nm, respectively.

It is common for the $\lambda_{PA}$ value to differ slightly from the corresponding $\lambda_{abs}$ based on empirical observation. Without being bound to theory, it was believed that since the appearance of both PA spectra feature sharp peaks characteristic of xanthene-based dyes, the XanthCR-880 exists predominantly in a non-aggregated state under these conditions. This is an important consideration because aggregates are associated with weaker PA signals owing to significant broadening of the absorbance band and a corresponding decrease of the molar absorptivity.

Next, it was established that there was a linear relationship between dye concentration and the PA signal up to the highest concentration tested (2.0 μM) and a limit of detection of 0.36 μM in ethanol (FIG. 3D).

Ideally PA contrast agents are photostable. When PA contrast agent are used in studies, they may be subjected to multiple imaging sessions, and as such are ideally resistant to photobleaching. When XanthCR-880 was continuously irradiated at its λPA for 60 min, it was found that the PA signal decreased by only 45%, indicating that XanthCR-880 is exceptionally photostable (FIG. 3E).

Spectral unmixing is a technique employed to isolate the signal of a PA contrast agent from that of other PA-active molecules such as hemoglobin found in blood. It was shown that this is possible using measurements with PA-active molecules in known concentrations and having well-defined PA spectrums. Typically, when newly developed dyes are tested for their PA properties, they are overlaid with a tissue mimicking phantom casted from agar containing 10% milk by volume. While this setup is efficient at scattering the incident light to provide even illumination of a sample, it lacks strong optical absorbers found in tissue that can attenuate light. As such, a better challenge to test the maximum attainable imaging depth was developed. FIG. 4 shows an integrated photoacoustic signal of XanthCR-880 (20 μM) in phosphate buffered saline (PBS) with 0.1% SDS overlaid with swine tissue with a thickness of 1, 2, 3, or 4 cm. Error=standard deviation. XanthCR-880 was placed in fluorinated ethylene propylene (FEP) tubing, overlaid with 1 cm thick agar-based tissue phantom and imaged at 25° C. In view of XanthCR-880 strong PA intensity in the NIR region, a robust signal could be detected even at tissue thickness of 4 cm (FIG. 4). This significant result demonstrates that XanthCR-880 possesses a substantially strong PA signal necessary for deep tissue PA imaging.

In conclusion, a new xanthene-based dye was developed using the D-A-D strategy with a thienylpiperidine unit, which is a strong donor, and the xanthene core as the acceptor. absX and Xem in the NIR I region was achieved and established that the dye is highly photostable. Furthermore, the dye is resistant to high concentration of glutathione and esterases, suggesting that it would be stable in biological environment. XanthCR-880 gave a weak emission signal; however, the PA signal was very intense and the $\lambda_{PA}$ is in the NIR region in organic and aqueous media. XanthCR-880 is compatible with multiple PA imaging systems and produced good PA signals even at depth of 4 cm in tissue. This is the longest wavelength xanthene-based PA dye to date.

REFERENCES (1) Wang, L. V.; Hu, S. Photoacoustic Tomography: In Vivo Imaging from Organelles to Organs. Science 2012, 335 (6075), 1458.

(2) Attia, A. B. E.; Balasundaram, G.; Moothanchery, M.; Dinish, U. S.; Bi, R.; Ntziachristos, V.; Olivo, M. A review of clinical photoacoustic imaging: Current and future trends. Photoacoustics 2019, 16, 100144.

(3) Teraphongphom, N.; Kong, C. S.; Warram, J. M.; Rosenthal, E. L. Specimen mapping in head and neck cancer using fluorescence imaging. Laryngoscope Investig Otolaryngol 2017, 2 (6), 447-452.

(4) Merkes, J. M.; Lammers, T.; Kancherla, R.; Rueping, M.; Kiessling, F.; Banala, S. Tuning Optical Properties of BODIPY Dyes by Pyrrole Conjugation for Photoacoustic Imaging. Adv. Opt. Mater. 2020, 8 (11), 1902115.

(5) Shi, B.; Gu, X.; Fei, Q.; Zhao, C. Photoacoustic probes for real-time tracking of endogenous H2S in living mice. Chemical Science 2017, 8 (3), 2150-2155.

(6) Ou, C.; Zhang, Y.; Ge, W.; Zhong, L.; Huang, Y.; Si, W.; Wang, W.; Zhao, Y.; Dong, X. A three-dimensional BODIPY-iron(iii) compound with improved H2O2-response for NIR-II photoacoustic imaging guided chemodynamic/photothermal therapy. Chem. Commun. 2020, 56 (46), 6281-6284.

(7) Zhou, E. Y.; Knox, H. J.; Liu, C.; Zhao, W.; Chan, J. A Conformationally Restricted Aza-BODIPY Platform for Stimulus-Responsive Probes with Enhanced Photoacoustic Properties. J. Am. Chem. Soc. 2019, 141 (44), 17601-17609.

(8) An, F.-F.; Deng, Z.-J.; Ye, J.; Zhang, J.-F.; Yang, Y.-L.; Li, C.-H.; Zheng, C.-J.; Zhang, X.-H. Aggregation-Induced Near-Infrared Absorption of Squaraine Dye in an Albumin Nanocomplex for Photoacoustic Tomography in Vivo. ACS Appl. Mater. Interfaces 2014, 6 (20), 17985-17992.

(9) Yao, D.; Wang, Y.; Zou, R.; Bian, K.; Liu, P.; Shen, S.; Yang, W.; Zhang, B.; Wang, D. Molecular Engineered Squaraine Nanoprobe for NIR-II/Photoacoustic Imaging and Photothermal Therapy of Metastatic Breast Cancer. ACS Appl. Mater. Interfaces 2020, 12 (4), 4276-4284.

(10) Lovell, J. F.; Jin, C. S.; Huynh, E.; Jin, H.; Kim, C.; Rubinstein, J. L.; Chan, W. C. W.; Cao, W.; Wang, L. V.; Zheng, G. Porphysome nanovesicles generated by porphyrin bilayers for use as multimodal biophotonic contrast agents. Nat. Mater. 2011, 10 (4), 324-332.

(11) Shimomura, K.; Kai, H.; Nakamura, Y.; Hong, Y.; Mori, S.; Miki, K.; Ohe, K.; Notsuka, Y.; Yamaoka, Y.; Ishida, M.; Kim, D.; Furuta, H. Bis-Metal Complexes of Doubly N-Confused Dioxohexaphyrins as Potential Near-Infrared-II Photoacoustic Dyes. J. Am. Chem. Soc. 2020, 142 (9), 4429-4437.

(12) Zheng, X.; Wang, L.; Liu, S.; Zhang, W.; Liu, F.; Xie, Z. Nanoparticles of Chlorin Dimer with Enhanced Absorbance for Photoacoustic Imaging and Phototherapy. Adv. Funct. Mater. 2018, 28 (26), 1706507.

(13) Merkes,J.M.; Rueping, M.;Kiessling,F.; Banala,S. Photoacoustic Detection of Superoxide Using Oxoporphyrinogen and Porphyrin. ACS Sensors 2019, 4 (8), 2001-2008.

(14) Li, X.; Tang, Y.; Li, J.; Hu, X.; Yin, C.; Yang, Z.; Wang, Q.; Wu, Z.; Lu, X.; Wang, W.; Huang, W.; Fan, Q. A small-molecule probe for ratiometric photoacoustic imaging of hydrogen sulfide in living mice. Chem. Commun. 2019, 55 (42), 5934-5937.

(15) Gao, W.; Li, X.; Liu, Z.; Fu, W.; Sun, Y.; Cao, W.; Tong, L.; Tang, B. A Redox-Responsive Self-Assembled Nanoprobe for Photoacoustic Inflammation Imaging to Assess Atherosclerotic Plaque Vulnerability. Anal. Chem. 2019, 91 (1), 1150-1156.

(16) Lu, Y.; Sun, Q.; Zhang, Z.; Tang, L.; Shen, X.; Xue, S.; Yang, W. New frog-type Dibenzo[a,c][1,2,5]thiadiazolo[3,4-i]phenazine heterocyclic derivatives with aggregation-enhanced one-and two-photon excitation NIR fluorescence. Dyes Pigm. 2018, 153, 233-240.

(17) Zhang, R.; Wang, Z.; Xu, L.; Xu, Y.; Lin, Y.; Zhang, Y.; Sun, Y.; Yang, G. Rational Design of a Multifunctional Molecular Dye with Single Dose and Laser for Efficiency NIR-II Fluorescence/Photoacoustic Imaging Guided Photothermal Therapy. Anal. Chem. 2019, 91 (19), 12476-12483.

(18) Jo, J.; Lee, C. H.; Kopelman, R.; Wang, X. In vivo quantitative imaging of tumor pH by nanosonophore assisted multispectral photoacoustic imaging. Nat. Commun. 2017, 8 (1), 471.

(19) Wang, S.; Yu, G.; Ma, Y.; Yang, Z.; Liu, Y.; Wang, J.; Chen, X. Ratiometric Photoacoustic Nanoprobe for Bioimaging of Cu2+. ACS Appl. Mater. Interfaces 2019, 11 (2), 1917-1923.

(20) Liu, F.; Shi, X.; Liu, X.; Wang, F.; Yi, H.-B.; Jiang, J.-H. Engineering an NIR rhodol derivative with spirocyclic ring-opening activation for high-contrast photoacoustic imaging. Chemical Science 2019, 10 (40), 9257-9264.

(21) Ikeno, T.; Hanaoka, K.; Iwaki, S.; Myochin, T.; Murayama, Y.; Ohde, H.; Komatsu, T.; Ueno, T.; Nagano, T.; Urano, Y. Design and Synthesis of an Activatable Photoacoustic Probe for Hypochlorous Acid. Anal. Chem. 2019, 91 (14), 9086-9092.

(22) Horvath, T. D.; Kim, G.; Kopelman, R.; Ashkenazi, S. Ratiometric photoacoustic sensing of pH using a "sonophore. Analyst 2008, 133 (6), 747-749.

(23) Kinnibrugh, T. L.; Salman, S.; Getmanenko, Y. A.; Coropceanu, V.; Porter, W. W.; Timofeeva, T. V.; Matzger, A. J.; Bredas, J.-L.; Marder, S. R.; Barlow, S. Dipolar Second-Order Nonlinear Optical Chromophores Containing Ferrocene, Octamethylferrocene, and Ruthenocene Donors and Strong π-Acceptors: Crystal Structures and Comparison of π-Donor Strengths. Organometallics 2009, 28 (5), 1350-1357.

(24) Qian, G.; Wang, Z. Y. Near-Infrared Organic Compounds and Emerging Applications. Chem. -Asian J. 2010, 5 (5), 1006-1029.

(25) Lu, Z.; Twieg, R. J. A mild and practical copper catalyzed amination of halothiophenes. Tetrahedron 2005, 61 (4), 903-918.

(26) Roger, J.; Doucet, H. Aryl triflates: useful coupling partners for the direct arylation of heteroaryl derivatives via Pd-catalyzed C—H activation—functionalization. Org. Biomol. Chem. 2008, 6 (1), 169-174.

(27) Rathnamalala, C. S. L.; Gayton, J. N.; Dorris, A. L.; Autry, S. A.; Meador, W.; Hammer, N. I.; Delcamp, J. H.; Scott, C. N. Donor-Acceptor-Donor NIR II Emissive Rhodindolizine Dye Synthesized by C—H Bond Functionalization. J. Org. Chem. 2019, 84 (20), 13186-13193.

(28) Matsui, M.; Yamamoto, T.; Kakitani, K.; Biradar, S.; Kubota, Y.; Funabiki, K. UV-vis absorption and fluorescence spectra, solvatochromism, and application to pH sensors of novel xanthene dyes having thienyl and thieno[3,2-b]thienyl rings as auxochrome. Dyes Pigm. 2017, 139, 533-540.

(29) Chai, J.-D.; Head-Gordon, M. Long-range corrected hybrid density functionals with damped atom—atom dispersion corrections. Phys. Chem. Chem. Phys. 2008, 10 (44), 6615-6620.

(30) Rappoport, D.; Furche, F. Property-optimized Gaussian basis sets for molecular response calculations. J. Chem. Phys. 2010, 133 (13), 134105.

(31) Humphrey, W.; Dalke, A.; Schulten, K. VMD: visual molecular dynamics. J. Mol. Graphics 1996, 14 (1), 33-38.

(32) Forman, H. J.; Zhang, H.; Rinna, A. Glutathione: overview of its protective roles, measurement, and biosynthesis. Mol. Aspects Med. 2009, 30 (1-2), 1-12.

(33) Kanazaki, K.; Sano, K.; Makino, A.; Takahashi, A.; Deguchi, J.; Ohashi, M.; Temma, T.; Ono, M.; Saji, H. Development of human serum albumin conjugated with near-infrared dye for photoacoustic tumor imaging. J. Biomed. Opt. 2014, 19 (9), 096002.

We claim:

1. A near infrared dye comprising a counterion and a structure of Formula I

Formula I

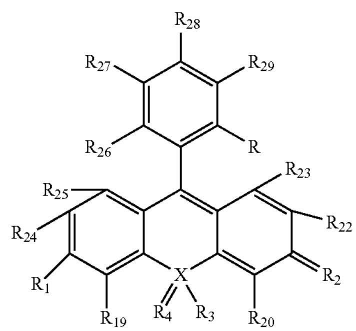

wherein X is selected from O, Si and P;

R is selected from hydrogen, —C(O)OH, a substituted or unsubstituted linear or branched $C_1$-$C_{18}$ alkyl group, a substituted or unsubstituted linear or branched $C_2$-$C_{18}$ alkenyl group, a substituted or unsubstituted $C_3$-$C_{10}$ cycloalkyl group, a substituted or unsubstituted linear or branched $C_1$-$C_{18}$ alkoxy group, an ester group represented by the formula —$C(O)OA^1$, wherein $A^1$ is a substituted or unsubstituted linear or branched $C_1$-$C_{18}$ alkyl group, a substituted or unsubstituted linear or branched $C_2$-$C_{18}$ alkenyl group or a substituted or unsubstituted $C_3$-$C_{10}$ cycloalkyl group, an amide group represented by the formula —$C(O)N(A^2)_2$, wherein $A^2$ is selected from a substituted or unsubstituted linear or branched $C_1$-$C_{18}$ alkyl group, a substituted or unsubstituted linear or branched $C_2$-$C_{18}$ alkenyl group, or a substituted or unsubstituted $C_3$-$C_{10}$ cycloalkyl group, or an ether group represented by the formula —$CH_2OA^3$ wherein $A^3$ is selected from a substituted or unsubstituted linear or branched $C_1$-$C_{18}$ alkyl group, a substituted or unsubstituted linear or branched $C_2$-$C_{18}$ alkenyl group, or a or a substituted or unsubstituted $C_3$-$C_{10}$ cycloalkyl group;

when X is O, then $R_3$ and $R_4$ are absent, and when X is Si, then $R_3$ and $R_4$ are each singly bonded to the Si atom, and are independently selected from hydrogen, a substituted or unsubstituted $C_1$-$C_{18}$ linear or branched alkyl group or a substituted or unsubstituted $C_3$-$C_{10}$ cycloalkyl group, when X is P, then $R_3$ is singly bonded to the P atom and is selected from hydrogen, a substituted or unsubstituted $C_1$-$C_{18}$ linear or branched alkyl group or a substituted or unsubstituted $C_3$-$C_{10}$ cycloalkyl group is P, and $R_4$ is singly bonded to the P and is a substituted or unsubstituted $C_1$-$C_{18}$ linear or branched alkyl group or a substituted or unsubstituted $C_3$-$C_{10}$ cycloalkyl group or $R_4$ is doubly bonded to the P and is an oxygen;

wherein $R_{19}$, $R_{20}$, $R_{22}$, $R_{23}$, $R_{24}$, $R_{25}$, $R_{26}$, $R_{27}$, $R_{28}$, and $R_{29}$ are each independently selected from hydrogen, sulfonate, halogen, hydroxy, amino, nitro, cyano, carboxy, an alkyl group having 1 to 20 carbon atoms, alkenyl group having 2 to 20 carbon atoms, alkynyl group having 2 to 20 carbon atoms, an aryl group having 6 to 10 carbon atoms, a heterocyclic group having 3 to 16 carbon atoms, an alkylether having 2 to 20 carbon atoms and 1 to 5 oxygen atoms, and an alkoxy group having 1 to 20 carbon atoms or wherein one or more pair of $R_{22}$ and $R_{23}$, $R_{24}$ and $R_{25}$, $R_{25}$ and $R_{26}$, $R_{26}$ and $R_{27}$, $R_{27}$ and $R_{28}$, $R_{28}$ and $R_{29}$, together with the carbons they are attached form a saturated or unsaturated 6 membered ring; and $R_1$ and $R_2$ are both selected from one of the following Groups A, B and C:

Group A $R_1$ is hydrogen and $R_2$ is a donor which is substituted or unsubstituted and is a 1-(thiophen-2-yl)piperidine, 1-(thieno[3,2-b]thiophen-2-yl)piperidine or 1-([2,2'-bithiophen]-5-yl)piperidine; or Group B both $R_1$ and $R_2$ are the same donors and both are substituted or unsubstituted, and are selected from 1-(thiophen-2-yl)piperidine, 1-(thieno[3,2-b]thiophen-2-yl)piperidine, and 1-([2,2'-bithiophen]-5-yl)piperidine; or Group C $R_1$ and $R_2$ are different donors and $R_1$ is a donor which is substituted or unsubstituted and is a 1-(thiophen-2-yl)piperidine, 1-(thieno[3,2-b]thiophen-2-yl)piperidine or 1-([2,2'-bithiophen]-5-yl)piperidine and $R_2$ is a donor which is substituted or unsubstituted and is selected from 1-(thiophen-2-yl)piperidine, 1-(thieno[3,2-b]thiophen-2-yl)piperidine, 1-([2,2'-bithiophen]-5-yl)piperidine, $C_2$-$C_{12}$ dialkyl amino, indolizine-3-yl, diphenylamino, and julolidinyl.

2. The NIR dye of claim 1, wherein X is O, and $R_3$ and $R_4$ are absent;

R is —C(O)OH, or

R is an ester group, an amide group, or an ether group and $A^1$, $A^2$, and $A^3$ are independently selected from a linear or branched CI-CB alkyl group, a linear or branched $C_2$-$C_{18}$ alkenyl group, or a $C_3$-$C_{10}$ cycloalkyl group that is substituted with 1 to 3 substituents independently selected from a halogen, sulfonate, hydroxy, amino, nitro, cyano, carboxy, an alkyl group having 1 to 20 carbon atoms, alkenyl group having 2 to 20 carbon atoms, alkynyl group having 2 to 20 carbon atoms, an aryl group having 6 to 10 carbon atoms, a heterocyclic group having 3 to 16 carbon atoms, and an alkoxy group having 1 to 20 carbon atoms.

3. The NIR dye of claim 1, wherein X is 0, and $R_3$ and $R_4$ are absent;

R is —C(O)OH or an ester group represented by the formula —$C(O)OA^1$ wherein $A^1$ is independently selected from a linear or branched $C_1$-$C_6$ alkyl group;

$R_1$ and $R_2$ are both selected from one of the following Groups A and B:

Group A $R_1$ is hydrogen and $R_2$ is a donor which is substituted with 0 to 3 substituents and is a 1-(thiophen-2-yl)piperidine, 1-(thieno[3,2-b]thiophen-2-yl)piperidine or 1-([2,2'-bithiophen]-5-yl)piperidine; or Group B both $R_1$ and $R_2$ are the same donors and both are substituted with 0 to 3 substituents, and are selected from 1-(thiophen-2-yl)piperidine group, 1-(thieno[3,2-b]thiophen-2-yl)piperidine, and 1-([2,2'-bithiophen]-5-yl)piperidine;

wherein the substituents are independently selected from a halogen, sulfonate, hydroxy, amino, nitro, cyano, carboxy, an alkyl group having 1 to 20 carbons, alkenyl group having 2 to 20 carbon atoms, alkynyl group having 2 to 20 carbon atoms, an alkylether having 2-20 carbon atoms and 1 to 5 oxygen atoms, an aryl group having 6 to 10 carbon atoms, a heterocyclic group having 3 to 16 carbons, and an alkoxy group having 1 to 20 carbon atoms.

4. The NIR dye of claim 1, wherein X is O, and $R_3$ and $R_4$ are absent;

R is —C(O)OH or an ester group represented by the formula —C(O)O$A^1$ wherein $A^1$ is independently selected from a linear or branched $C_1$-$C_6$ alkyl group;

$R_1$ and $R_2$ are both selected from Group C:

Group C $R_1$ and $R_2$ are different donors and $R_1$ is a donor which is substituted with 0 to 3substituents and is a 1-(thiophen-2-yl)piperidine, 1-(thieno[3,2-b]thiophen-2-yl)piperidine or 1-([2,2'-bithiophen]-5-yl)piperidine and $R_2$ is a donor which is substituted with 0 to 3 substituents, and is selected from 1-(thiophen-2-yl)piperidine, 1-(thieno[3,2-b]thiophen-2-yl)piperidine, 1-([2,2'-bithiophen]-5-yl)piperidine, $C_2$-$C_{12}$ dialkyl amino, indolizine-3-yl, diphenylamino, and julolidinyl;

wherein the substituents are independently selected from a halogen, sulfonate, hydroxy, amino, nitro, cyano, carboxy, an alkyl group having 1 to 20 carbon atoms, alkenyl group having 2 to 20 carbon atoms, alkynyl group having 2 to 20 carbon atoms, an alkylether having 2 to 20 carbon atoms and 1 to 5 oxygen atoms, an aryl group having 6 to 10 carbon atoms, a heterocyclic group having 3 to 16 carbon atoms, and an alkoxy group having 1 to 20 carbon atoms.

5. The NIR dye of claim 1, wherein X is O, and $R_3$ and $R_4$ are absent;

R is —C(O)OH or an ester group represented by the formula —C(O)O$A^1$ wherein $A^1$ is independently selected from a linear or branched $C_1$-$C_6$ alkyl group;

$R_1$ and $R_2$ are both selected from Group C:

Group C $R_1$ and $R_2$ are different donors and $R_1$ is a donor which is substituted with 0 to 3 substituents and is a 1-(thiophen-2-yl)piperidine, 1-(thieno[3,2-b]thiophen-2-yl)piperidine or 1-([2,2'-bithiophen]-5-yl)piperidine and $R_2$ is a donor which is substituted with 0 to 3 substituents and is selected from 1-(thiophen-2-yl)piperidine, 1-(thieno[3,2-b]thiophen-2-yl)piperidine, 1-([2,2'-bithiophen]-5-yl)piperidine, diethyl amino, and julolidinyl;

wherein the substituents are independently selected from a halogen, sulfonate, hydroxy, amino, nitro, cyano, carboxy, an alkyl group having 1 to 20 carbon atoms, alkenyl group having 2 to 20 carbon atoms, alkynyl group having 2 to 20 carbon atoms, an alkylether having 2 to 20 carbon atoms and 1 to 5 oxygen atoms, an aryl group having 6 to 10 carbon atoms, a heterocyclic group having 3 to 16 carbon atoms, and an alkoxy group having 1 to 20 carbon atoms.

6. The NIR dye of claim 1, wherein the counterion is nitrite, sulfate, phosphate, bicarbonate, trifluoroacetate, pentafluoropropanoate, chloride, bromide, iodide, perchlorate, nitrate, benzenesulfonate, p-toluenesulfonate, methyl sulfate, ethyl sulfate, propyl sulfate, tetrafluoroborate, tetraphenylborate, hexafluorophosphate, benzenesulfinate, acetate, trifluoroacetate, propionacetate, benzoate, oxalate, succinate, malonate, oleate, stearate, citrate, monohydrogen diphosphate, dihydrogen monophosphate, pentachlorostannate, chlorosulfonate, fluorosulfonate, trifluoromethansulfonate, hexafluoroarsenate, hexafluoroantimonate, molybdenate, tungstate, titanate, zirconate ions, or any combination thereof.

7. The NIR dye of claim 1, wherein the counterion is trifluoroacetate, pentafluoropropanoate, chloride, bromide, iodide, fluorosulfonate, and trifluoromethansulfonate.

8. The NIR dye of claim 1, wherein $R_{19}$, $R_{20}$, $R_{22}$, $R_{23}$, $R_{24}$, $R_{25}$, $R_{26}$, $R_{27}$, $R_{28}$, and $R_{29}$ are each independently selected from hydrogen, sulfonate, halogen, hydroxy, amino, nitro, cyano, carboxy, an alkyl group having 1 to 6 carbon atoms, alkenyl group having 2 to 6 carbon atoms, an alkylether having 2 to 20 carbon atoms and 1 to 5 oxygen atoms, an aryl group having 6 to 10 carbon atoms, a heterocyclic group having 6 to 10 carbon atoms, and wherein 0 or 1 pair of $R_{22}$ and $R_{23}$, $R_{24}$ and $R_{25}$, $R_{25}$ and $R_{26}$, $R_{26}$ and $R_{27}$, $R_{27}$ and $R_{28}$, $R_{28}$ and $R_{29}$, together with the carbons they are attached from form a saturated or unsaturated 6 membered ring.

9. The NIR dye of claim 1, wherein $R_{19}$, $R_{20}$, $R_{22}$, $R_{23}$, $R_{24}$, $R_{25}$, $R_{26}$, $R_{27}$, $R_{28}$, and $R_{29}$ are each independently selected from hydrogen, halogen, hydroxy, an alkyl group having 1 to 6 carbon atoms, and a phenyl.

10. The NIR dye of claim 1, wherein $R_{19}$, $R_{20}$, $R_{22}$, $R_{23}$, $R_{24}$, $R_{25}$, $R_{26}$, $R_{27}$, $R_{28}$, and $R_{29}$ are each hydrogen.

11. The NIR dye of claim 1, wherein the NIR dye has one of the following structures:

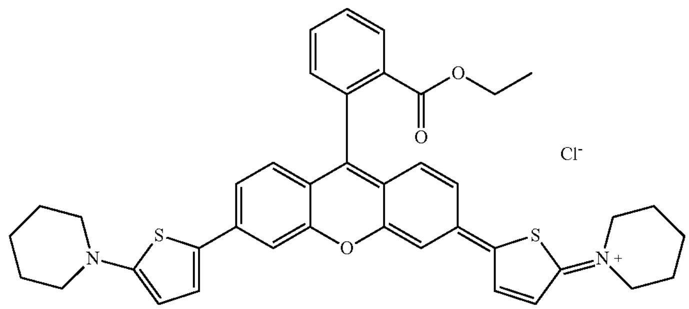

,

XanthCR-880

-continued

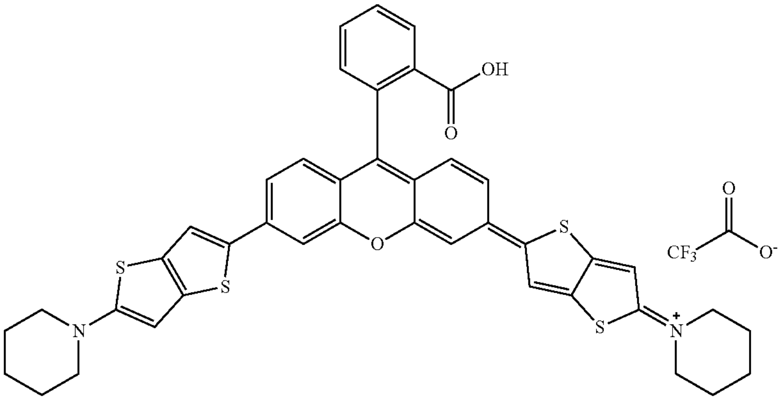

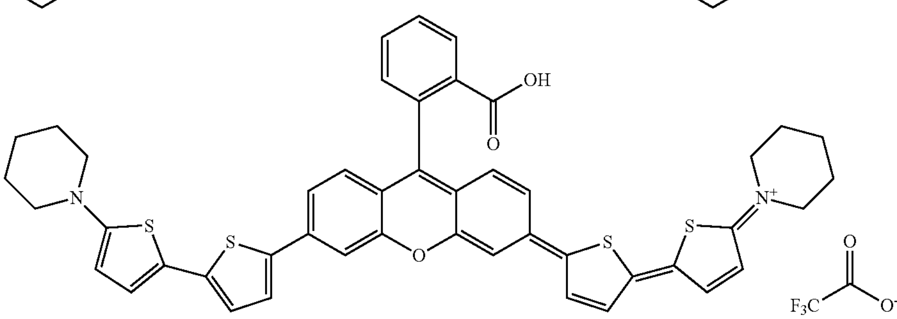

,

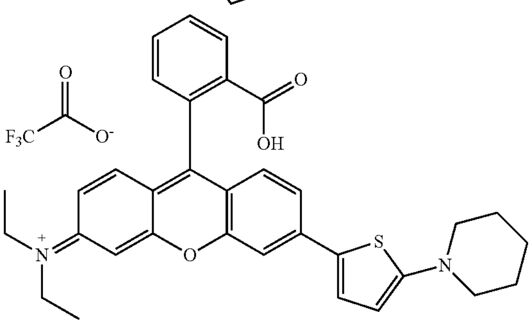

,

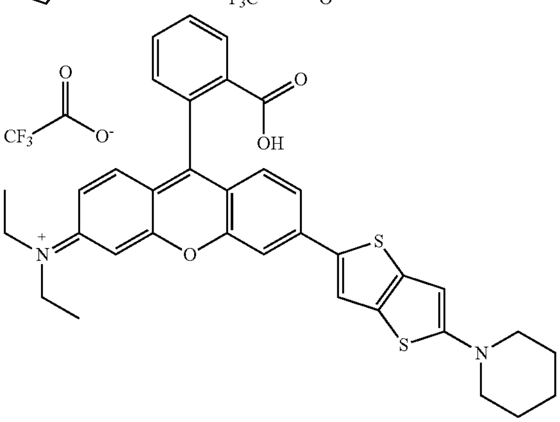

, and

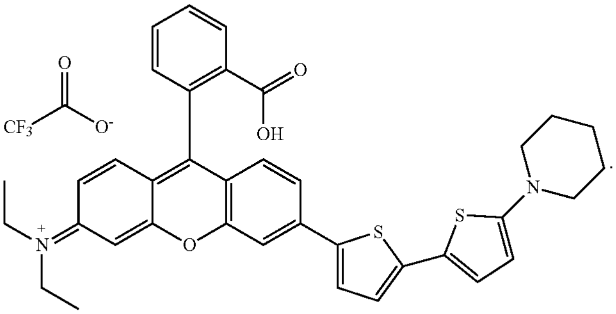

12. The NIR dye of claim 1, wherein the NIR dye absorbs light in the NIR I region and/or the NIR II region; or wherein the NIR dye absorbs light in the NIR II region; or wherein the NIR dye has an absorption maximum in the NIR II region.

13. A composite comprising the NIR dye of claim 1 in a polymer matrix.

14. The composite according to claim 13, wherein the polymer matrix is solid at room temperature.

15. A composition comprising the NIR dye of claim 1 and a pharmaceutically-acceptable carrier or a solid polymer matrix.

16. A method for making a NIR dye, the method comprising:

(a) performing a C—H arylation reaction by combining a Donor and an Acceptor of Formula II with a catalyst selected from the group consisting of bis(triphenylphosphine)palladium(II) dichloride, palladium(II)

acetate, tris(dibenzylideneacetone)dipalladium(O), $CHCl_3$,or any combination thereof, in a solvent to form a reaction mixture, Formula II

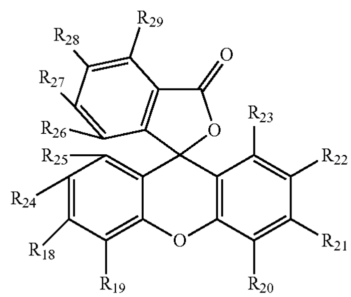

wherein $R_{18}$ and $R_{21}$ are individually selected from Cl, Br, I and $OSO_2R_{52}$ wherein $R_{52}$ is a hydrogen or lower alkyl;

wherein $R_{19}$, $R_{20}$, $R_{22}$, $R_{23}$, $R_{24}$, $R_{25}$, $R_{26}$, $R_{27}$, $R_{28}$, and $R_{29}$ are each independently selected from hydrogen or an alkyl group having 1 to 20 carbons, or wherein one or more pair of $R_{22}$ and $R_{23}$, $R_{24}$ and $R_{25}$, $R_{25}$ and $R_{26}$, $R_{26}$ and $R_{27}$, $R_{27}$ and $R_{28}$, $R_{28}$ and $R_{29}$, together with the carbons they are attached form a saturated or unsaturated 6 membered ring; and wherein the Donor(s) is substituted or unsubstituted and comprises at least one from Group (X) and one from Group (Y):

(X) 1-(thiophen-2-yl)piperidine, 1-(thieno[3,2-b]thiophen-2-yl)piperidine or 1-([2,2'-bithiophen]-5-yl)piperidine; and (Y) 1-(thiophen-2-yl)piperidine, 1-(thieno[3,2-b]thiophen-2-yl)piperidine, 1-([2,2'-bithiophen]-5-yl)piperidine, $C_2$-$C_{12}$ dialkyl amine, indolizine, diphenylamine, and julolidine, to thereby replace the groups at $R_{18}$ and $R_{21}$ with said Donor(s);

(b) a ring opening reaction by transesterification with an alcohol to give the NIR dye of Formula I Formula I

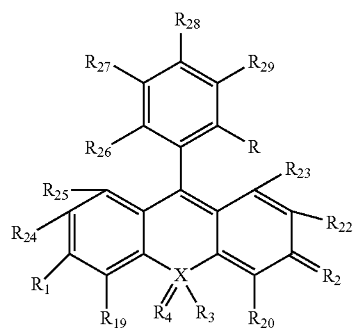

wherein X is O, and $R_3$ and $R_4$ are absent;

R is selected from —C(O)OH or an ester group represented by the formula —C(O)OA[1], wherein A[1] is a linear or branched $C_1$-$C_{18}$ alkyl group;

wherein $R_{19}$, $R_{20}$, $R_{22}$, $R_{23}$, $R_{24}$, $R_{25}$, $R_{26}$, $R_{27}$, $R_{28}$, and $R_{29}$ are as described above; and $R_1$ and $R_2$ are both selected from one of the following Groups B and C:

Group B both $R_1$ and $R_2$ are the same donors and both are substituted or unsubstituted, and are selected from 1-(thiophen-2-yl)piperidine group, 1-(thieno[3,2-b]thiophen-2-yl)piperidine, and 1-([2,2'-bithiophen]-5-yl)piperidine; or Group C $R_1$ and $R_2$ are different donors and $R_1$ is a donor which is substituted or unsubstituted and is a 1-(thiophen-2-yl)piperidine, 1-(thieno[3,2-b]thiophen-2-yl)piperidine or 1-([2,2'-bithiophen]-5-yl)piperidine and $R_2$ is a donor which is substituted or unsubstituted and is selected from 1-(thiophen-2-yl)piperidine, 1-(thieno[3,2-b]thiophen-2-yl)piperidine, 1-([2,2'-bithiophen]-5-yl)piperidine, $C_2$-$C_{12}$ dialkyl amino, indolizine-3-yl, diphenylamino, and julolidinyl.

17. The method for making a NIR dye of claim 16, wherein the catalyst in step (a) is a palladium compound.

18. The method for making a NIR dye of claim 16, wherein the compound of Formula II is as follows:

2

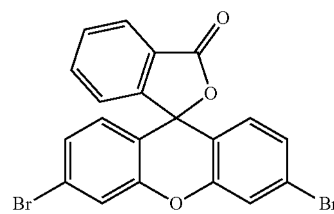

19. The method for making a NIR dye of claim 16, wherein the compound formed in step (a) has the following structure:

3

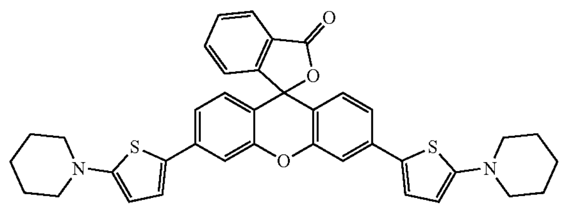

20. A method for imaging a biological sample, the method comprising:

(a) contacting the biological sample with an effective amount of the composition of claim 15;

(b) exposing the biological sample and the composition to NIR radiation; and (c) observing photoacoustic resonance or fluorescence in the biological sample.

* * * * *